US009840457B2

(12) United States Patent
Bradley et al.

(10) Patent No.: US 9,840,457 B2
(45) Date of Patent: Dec. 12, 2017

(54) LYSINE ISOTOPOLOGUES, COMPOSITIONS COMPRISING THE SAME AND METHODS OF SYNTHESIS

(71) Applicant: Cambridge Isotope Laboratories, Inc., Tewksbury, MA (US)

(72) Inventors: Joel Chandler Bradley, Cambridge, MA (US); William Wakefield Wood, Andover, MA (US); Salim Barkallah, Tewksbury, MA (US); William James Ryan, Westford, MA (US); Richard Charles Titmas, Boxford, MA (US); Mark Donald Schwinden, Derry, NH (US); Janusz Konrad Kozak, Methuen, MA (US); Marwan ElMasri, Groton, MA (US); Steven Michael Torkelson, Lawrence, MA (US)

(73) Assignee: Cambridge Isotope Laboratories, Inc., Tewksbury, MA (US)

( * ) Notice: Subject to any disclaimer, the term of this patent is extended or adjusted under 35 U.S.C. 154(b) by 0 days.

(21) Appl. No.: 14/773,284

(22) PCT Filed: Mar. 12, 2014

(86) PCT No.: PCT/US2014/024513
§ 371 (c)(1),
(2) Date: Sep. 4, 2015

(87) PCT Pub. No.: WO2014/150909
PCT Pub. Date: Sep. 25, 2014

(65) Prior Publication Data
US 2016/0016890 A1    Jan. 21, 2016

Related U.S. Application Data

(60) Provisional application No. 61/801,242, filed on Mar. 15, 2013.

(51) Int. Cl.
*C07C 229/26*    (2006.01)
*C07B 59/00*    (2006.01)
*A23K 20/142*    (2016.01)
*A23K 50/50*    (2016.01)

(52) U.S. Cl.
CPC .......... *C07C 229/26* (2013.01); *A23K 20/142* (2016.05); *A23K 50/50* (2016.05); *C07B 59/001* (2013.01); *C07B 2200/05* (2013.01)

(58) Field of Classification Search
CPC .. C07C 229/26; C07B 2200/05; C07B 59/001
See application file for complete search history.

(56) References Cited

U.S. PATENT DOCUMENTS

2004/0024307 A1    2/2004   Golman et al.
2011/0082208 A1    4/2011   Shchepinov

FOREIGN PATENT DOCUMENTS

WO    WO-2008/125957    10/2008

OTHER PUBLICATIONS

Inbar et al, European Journal of Biochemistry, 13C-NMR, 1 H-NMR and gas chromatography mass-spectrometry studies of the biosynthesis of 13C-enriched L-lysine by Brevihacterium flavum,1983, 162, pp. 621-633.*
CRC, CRC Handbook of Chemistry and Physics, 1989, CRC Press, Inc., Boca Raton, FL, pp. B-228-B-229.*
Kainosho et al, European Journal of Biochemistry, 13C-NMR, 1 H-NMR and gas chromatography mass-spectrometry studies of the biosynthesis of 13C-enriched L-lysine by Brevihacterium flavum,1983, 162, pp. 621-633.*
International Preliminary Report on Patentability for PCT Appl. Ser. No. PCT/US2014/024513 dated Sep. 24, 2015.
Inbar et al. 13C-NMR, 1 H-NMR and gas-chromatography mass-spwtromtry studies of the biosynthesis of 13C-enriched L-lysine by Brevibacterium flavum, Eur. J. Biochem. 162(3): 621-633, 1987. [retrieved on Aug. 11, 2014) Retrieved from the Internet. <URL: http://onlinelibrary.wiley.com/doi/10.1111{j.1432-1033.1987. tb10684.x/pdf> entire document.
International Search Report and Written Opinion for PCT Appl. Ser. No. PCT/US2014/024513 dated Aug. 27, 2014 (12 pages).

* cited by examiner

*Primary Examiner* — Paul A Zucker
(74) *Attorney, Agent, or Firm* — Foley & Lardner LLP; James F. Ewing

(57) ABSTRACT

This invention relates to lysine isotopologues of Formulas I and 1-A, as described herein, and processes for synthesizing the same and derivatives and intermediates involved therein. In one aspect, described herein is a chemical compound comprising an isotopically labeled analog, i.e., an isotopologue of a standard or naturally occurring lysine. The lysine isotopologue is synthetically formed to have stable isotopes of elements incorporated at selected positions. As such, the lysine isotopologue has a molecular mass different from the mass of a standard or naturally occurring lysine.

21 Claims, No Drawings

LYSINE ISOTOPOLOGUES, COMPOSITIONS COMPRISING THE SAME AND METHODS OF SYNTHESIS

RELATED APPLICATIONS

This application is the U.S. National Stage of International Application Number PCT/US2014/024513, filed Mar. 12, 2014, which claims priority to U.S. Provisional Application No. 61/801,242, filed Mar. 15, 2013, the entire contents of which are incorporated herein by reference.

BACKGROUND

Lysine is a naturally occurring amino acid. Non-natural isotopologues of lysine and methods of making the same are needed.

SUMMARY

In one aspect, described herein is a chemical compound comprising an isotopically labeled analog, i.e., an isotopologue of a standard or naturally occurring lysine. The lysine isotopologue is synthetically formed to have stable isotopes of elements incorporated at selected positions. As such, the lysine isotopologue has a molecular mass different from the mass of a standard or naturally occurring lysine. In various aspects, provided herein are lysine isotopologues, and particularly L-lysine isotopologues, compositions comprising the same, polypeptides derived from lysine isotopologues, associated kits and processes for the syntheses of lysine isotopologues and intermediates thereto.

This invention relates generally to compounds of Formula I or I-A

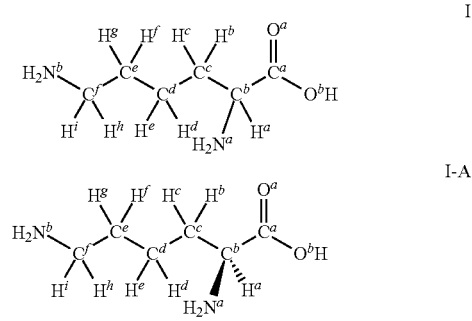

or a salt or derivative thereof, wherein
each $H^a$, $H^b$, $H^c$, $H^d$, $H^e$, $H^f$, $H^g$, $H^h$, and $H^i$ is independently $^1H$ or $^2H$;
each $C^a$, $C^b$, $C^c$, $C^d$, $C^e$ and $C^f$ is independently $^{12}C$ or $^{13}C$; and at least two of $C^a$, $C^b$, $C^c$, $C^d$, $C^e$ and $C^f$ are $^{13}C$;
each $N^a$ and $N^b$ is independently $^{14}N$ or $^{15}N$; and
$O^a$ and $O^b$ are both $^{16}O$ or $^{18}O$;
with the provision that the compound is not:
2,3,3,4,4,5,5,6,6-$D_9$-L-lysine; 3,3,4,4,5,5,6,6-$D_8$-L-lysine; 1,2,3,4,5,6-$^{13}C_6$-L-lysine; 1,2,3,4,5,6-$^{13}C_6$,$^{15}N_2$-L-lysine; 4,4,5,5-$D_4$-L-lysine or 1,2-$^{13}C_2$-L-lysine.

In another aspect, a composition is provided, where the composition comprising two or more different compounds of Formula I, as described herein, wherein
each of the compounds has a gross mass difference relative to the mass of naturally occurring lysine;
the gross mass difference relative to lysine is the same for all of the compounds; and
the gross mass difference is an integer of 4 to 12.

In another aspect, a polypeptide is provided, where the polypeptide comprises any of the compounds of Formula I, as described herein.

In another aspect, an edible composition is provided, where the edible composition comprises any of the compounds of Formula I, compositions comprising the compounds of Formula I and/or the polypeptides derived from the compounds of Formula I, as described herein. In some embodiments, the edible composition is a food for mice.

In another aspect, a mouse is provided, wherein the mouse comprises lysine, and wherein between 1% and 99% of the lysine derives from the lysine isotopologue of Formula I or I-A.

In another aspect, a kit is provided, where the kit comprises any of the compounds described herein. In another aspect, a kit is provided, where the kit comprises any of the compositions described herein. In another aspect, a kit is provided, where the kit comprises any of the edible compositions described herein.

In yet another aspect, a process for preparing a compound of Formula I or I-A, as described herein, is provided.

DETAILED DESCRIPTION

It is to be understood that this invention is not limited to particular embodiments described. It is also to be understood that the terminology used herein is for the purpose of describing particular embodiments only, and is not intended to be limiting, since the scope described herein will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients.

Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope as described herein.

The term "about" when used before a numerical designation, e.g., temperature, time, amount, and concentration, including range, indicates approximations which may vary by (+) or (−) 10%, 5%, or 1%.

The term "halo" or "halo group" refers to fluoro, chloro, bromo and iodo.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

As used herein, $C_m$-$C_n$, such as $C_1$-$C_{10}$, $C_1$-$C_6$, or $C_1$-$C_4$ when used before a group refers to that group containing m to n carbon atoms.

The term "alkyl" refers to monovalent saturated aliphatic hydrocarbyl groups having from 1 to 10 carbon atoms (i.e., $C_1$-$C_{10}$alkyl) or 1 to 6 carbon atoms (i.e., $C_1$-$C_6$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), and n-butyl ($CH_3CH_2CH_2CH_2$—). In some embodiments, the term "alkyl" refers to substituted or unsubstituted, straight chain or branched alkyl groups with $C_1$-$C_{12}$, $C_1$-$C_6$ and preferably $C_1$-$C_4$ carbon atoms.

The term "protecting group" refers to an "amino protecting group" if attached to a nitrogen atom, an "hydroxyl protecting group" if attached to an oxygen atom of an alcohol group, a "carboxylic acid protecting group" if attached to an oxygen atom of a carboxylate group. Protecting groups, as described in more detail below, are well known in the art and include those described in detail in *Protecting Groups in Organic Synthesis*, T. W. Greene and P. G. M. Wuts, 4$^{th}$ edition, John Wiley & Sons, 2006, the entirety of which is incorporated herein by reference.

An "amino protecting group," as used herein, is well known in the art and include those described in detail in Greene (2006). Suitable non-limiting amino-protecting groups include methyl carbamate, ethyl carbamante, 9-fluorenylmethyl carbamate (Fmoc), t-butyl carbamate (BOC), and benzyl carbamate (Cbz).

A "carboxylic acid protecting group," or "protected carboxylic acid," as used herein, are well known in the art and include those described in detail in Greene (2006). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "hydroxyl protecting group" as used herein, is well known in the art and include those described in detail in Greene (2006). Suitable hydroxyl protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), 2-methoxyethoxymethyl (MEM), tetrahydropyranyl (THP), trimethylsilyl (TMS), triethylsilyl (TES), triisopropylsilyl (TIPS), diphenylmethylsilyl (DPMS), t-butylmethoxyphenylsilyl (TBMPS), formate, benzoylformate, acetate, chloroacetate, dichloroacetate, trichloroacetate, trifluoroacetate, 9-fluorenylmethyl carbonate (Fmoc), methanesulfonate (mesylate), benzylsulfonate, and tosylate (Ts).

The term "leaving group" or "LG" as used herein, is well known among those of skill in the art as a labile substituent of a compound that is readily displaced from the compound. Leaving groups, as used herein, are described in *March's Advanced Organic Chemistry*, (John Wiley, and Sons, 5$^{th}$ Edition, 2001), and encompass the group consisting of a halo or $O(SO_2)R^A$; where each $R^A$ is, independently, alkyl or aryl. In certain embodiments, each leaving group is, independently, a chloro; bromo; iodo;

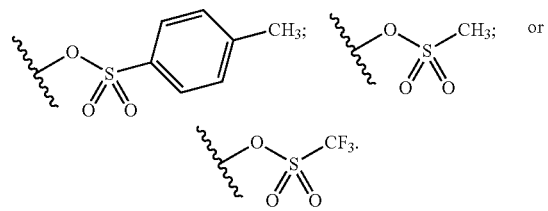

The term "hydrolyzing" refers to adding water across a C—O and/or a C—S bond, such as hydrolyzing a ketal, a thioketal and the likes to the corresponding ketone. A hydrolysis is performed using various methods well known to the skilled artisan, non limiting examples of which include acidic hydrolysis. A variety of acids such as protic acids and Lewis acids can be used for the hydrolysis.

The term "oxidizing" or "oxidation" refers to taking one or more electron away from a bond or an atom, preferably taking two electrons away from a bond or an atom. Non-limiting examples of oxidation include conversion of an alcohol to an aldehyde.

The term "reducing" or "reduction" refers to adding one or more electron across a bond or an atom, preferably adding two electrons to a bond or an atom. Non-limiting examples of reduction include conversion of a carboxylic acid or an ester thereof to an alcohol.

The term "salt" refers to an ionic compound formed between an acid and a base. A salt of a compound disclosed herein is formed between an acid and a basic group of the compound, such as an amino functional group, or a base and an acidic group of the compound, such as a carboxyl functional group. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, $NH_4$, Ca, Ba, imidazolium, and ammonium cations based on naturally occurring amino acids. When the compounds provided and/or utilized herein contain basic functionality, such salts include, without limitation, salts of organic acids, such as caroboxylic acids and sulfonic acids, and mineral acids, such as hydrogen halides, sulfuric acid, phosphoric acid, and the likes.

The terms "isotopologue" or "stable isotope labeled lysine compound" refer to a species that differs from a specific compound disclosed herein only in the isotopic composition thereof.

The term "naturally occurring" as it pertains to lysine refers to lysine having a natural abundance of a specified isotope or of all the isotopes in the lysine compound. By contrast, the lysine isotopologues described herein are not naturally occurring.

The term "isotopic enrichment factor" as used herein means the ratio between the isotopic abundance and the natural abundance of a specified isotope.

In other embodiments, a compound as described herein has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term that one substance is "substantially free" of a second substance indicates that there is less than 2 wt %, 1 wt %, 0.01 wt %, 0.001 wt % or 0.00001 wt % of the second substance present with the first substance. Alternatively, the second substance may be undetectable by conventional means in the first substance.

The term "exact mass difference," as used herein, refers to the exact mass difference, expressed to at least three decimal places, (e.g., 0.005), between naturally occurring lysine and a non-naturally occurring isotopologue of lysine, such as those described herein.

The term "gross mass difference," as used herein, refers to the gross mass difference, expressed as an integer, (e.g., 4, 6, or 8) between naturally occurring lysine and a non-naturally occurring isotopologue of lysine, such as those described herein.

The compounds described herein (e.g., compounds of Formula I), may contain an asymmetric carbon atom, for example, as the result of deuterium substitution or otherwise. As such, compounds as described herein can exist as either individual enantiomers, or mixtures of the two enantiomers. Accordingly, a compound described herein will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein.

Both "$^2$H" and "D" refer to deuterium.

"Stereoisomer" refers to both enantiomers and diastereoisomers.

The natural abundance of various isotopes in nature has been approximated, for example, in the CRC Handbook of Chemistry and Physics, published by CRC Press, Inc.

The most abundantly occurring form of carbon, the carbon-12 ($^{12}$C) isotope, is approximately 98.90% abundant in nature. The stable carbon-13 ($^{13}$C) isotope, by contrast, is only approximately 1.10% naturally abundant. Other isotopes of carbon are even less abundant, and many undergo radioactive decay. The most abundantly occurring isotope of hydrogen ($^1$H) is approximately 99.985% abundant in nature. The stable isotope deuterium ($^2$H), by contrast, is only approximately 0.015% naturally abundant. Various stable isotopes of nitrogen and oxygen exist in nature, as well. For example, $^{14}$N and $^{15}$N are 99.63% and 0.37% naturally abundant, respectively; $^{16}$O, $^{17}$O and $^{18}$O are 99.76%, 0.04% and 0.20% naturally abundant, respectively.

Accordingly, standard lysine compounds known in the art will generally have incorporated therein various isotopes in these respective percentages of natural abundance. The present invention, however, provides analogs of such standard lysines in which the less naturally abundant stable isotopes are selectively incorporated into the lysine structure at desired positions thereof, such that a given analog will have a characteristic molecular weight different from the molecular weight of its corresponding standard or naturally occurring lysines and derivatives thereof.

The present disclosure is broadly directed to new chemical compounds, namely stable isotope labeled lysines. In particular, the present invention provides isotopically labeled analogs of standard lysines, wherein a given isotopically labeled analog has incorporated therein at a selected position in the structure thereof a stable, or non-radioactive, isotope having a mass different from the mass of the most abundantly occurring isotope of the appropriate element in nature. A given analog can be differentiated from its corresponding standard lysine (one having primarily only the most naturally abundant isotopes incorporated therein) using methods such as mass spectrometric analysis, given the molecular weight differences between the isotopically labeled analog and its corresponding standard lysine or lysine derivative (e.g., polypeptide).

Lysine Isotopologue Compounds

The stable isotope labeled compounds described herein are demonstrably useful for labeling proteins in cell culture and animals. They are also demonstrably useful for generating stable isotopically labeled protein and peptide standards to identify and quantify proteins in cell culture, animal and human experiments. For example, the stable isotope labeled lysine compounds can be added to cell culture for incorporation into proteins. Alternatively, the stable isotope labeled lysine compounds can be added to animal feed or rodent feed, such as mouse feed or "chow," and fed to the mouse. The mouse can then be sacrificed and the extent can be determined to which the stable isotope labeled lysine compounds, as described herein, have been incorporated into the mouse.

In some aspects, a compound is provided of Formula I:

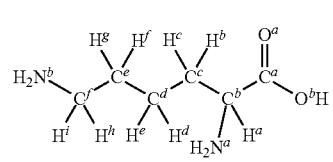

or a salt or derivative thereof, wherein each $H^a$, $H^b$, $H^c$, $H^d$, $H^e$, $H^f$, $H^g$, $H^h$, and $H^i$ is independently $^1$H or 2H;

each $C^a$, $C^b$, $C^c$, $C^d$, $C^e$ and $C^f$ is independently $^{12}$C or $^{13}$C; and at least two of $C^a$, $C^b$, $C^c$, $C^d$, $C^e$ and $C^f$ are $^{13}$C;

each $N^a$ and $N^b$ is independently $^{14}$N or $^{15}$N; and $O^a$ and $O^b$ are both $^{16}$O or $^{18}$O;

with the provision that the compound is not:
2,3,3,4,4,5,5,6,6-$D_9$-L-lysine; 3,3,4,4,5,5,6,6-$D_8$-L-lysine; 1,2,3,4,5,6-$^{13}C_6$-L-lysine; 1,2,3,4,5,6-$^{13}C_6$,$^{15}N_2$-L-lysine; 4,4,5,5-$D_4$-L-lysine or 1,2-$^{13}C_2$-L-lysine.

In one embodiment, the compound is of Formula I-A:

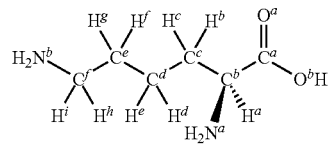

I-A or a salt or derivative thereof.

In some embodiments, $C^c$, $C^d$ and $C^e$ are $^{13}C$. In some embodiments, at least four of $C^a$, $C^b$, $C^c$, $C^d$, $C^e$ and $C^f$ are $^{13}C$. In some embodiments, $C^b$, $C^c$, $C^d$ and $C^e$ are $^{13}C$. In some embodiments, $C^c$, $C^d$, $C^e$ and $C^f$ are $^{13}C$. In some embodiments, at least five of $C^a$, $C^b$, $C^c$, $C^d$, $C^e$ and $C^f$ are $^{13}C$. In some embodiments, $C^a$, $C^b$, $C^d$, $C^d$ and $C^e$ are $^{13}C$. In some embodiments, $C^b$, $C^c$, $C^d$, $C^e$ and $C^f$ are $^{13}C$.

In some embodiments, at least two of $H^a$, $H^b$, $H^c$, $H^d$, $H^e$, $H^f$, $H^g$, $H^h$ and $H^i$ are $^2H$. In some embodiments, $H^g$ and $H^f$ are $^2H$. In some embodiments, $H^h$ and $H^i$ are $^2H$. In some embodiments, at least four of $H^a$, $H^b$, $H^c$, $H^d$, $H^e$, $H^f$, $H^g$, $H^h$ and $H^i$ are $^2H$. In some embodiments, $H^f$ $H^g$, $H^h$ and $H^i$ are $^2H$. In some embodiments, at least six of $H^a$, $H^b$, $H^c$, $H^d$, $H^e$, $H^f$, $H^g$, $H^h$ and $H^i$ are $^2H$.

In some embodiments, $N^a$ is $^{15}N$. In some embodiments, $N^b$ is $^{15}N$. In some embodiments, $N^a$ and $N^b$ are $^{15}N$.

In some embodiments, the compound is of Formula

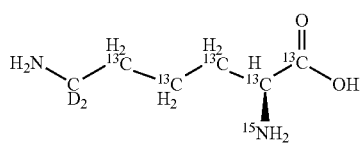

II

L-Lysine (1,2,3,4,5-$^{13}C_5$, 2-$^{15}N$, 6,6-$D_2$)

or a salt or derivative thereof.

In some embodiments, the compound is of Formula

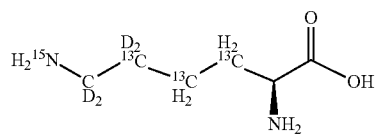

III

L-Lysine (3,4,5-$^{13}C_3$, 6-$^{15}N$, 5,5,6,6-$D_4$)

or a salt or derivative thereof.

In some embodiments, the compound is of Formula

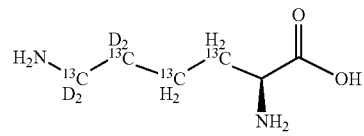

IV

L-Lysine (3,4,5,6-$^{13}C_4$, 5,5,6,6-$D_4$)

or a salt or derivative thereof.

In some embodiments, the compound is of Formula

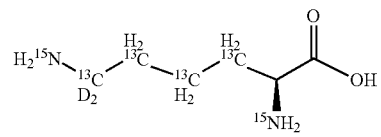

V

L-Lysine (3,4,5,6-$^{13}C_4$, 2, 6-$^{15}N_2$ 6,6-$D_2$)

or a salt or derivative thereof.

In any of the embodiments, the derivative of the compound is an amide, ester, guanidine, amidine, acetate or carbamate. In some embodiments, the ester is a methyl or ethyl ester. In some embodiments, the acetate is a trifluoroacetate.

Compositions Comprising the Lysine Isotopologue Compounds

The compositions described herein, having stable isotope labeled lysine compounds, are demonstrably useful for multiplexed protein labeling experiments in cell culture (e.g., SILAC) and in animals.

As noted above, the stable isotope labeled lysine compounds can also be added to animal feed or rodent feed, such as mouse feed or "chow," and fed to the mouse. The mouse can then be sacrificed and the extent can be determined to which the stable isotope labeled lysine compounds, as described herein, have been incorporated into the mouse. Thus, in some embodiments, the composition described herein may further include animal food. In some embodiments, the compositions further include mouse food, i.e., "chow." These compositions may also include additional lysine compounds that are outside the scope of the lysine compounds of Formula I as described herein.

Thus, in another aspect, a composition is provided, where the composition comprises two or more different compounds of Formula I or I-A:

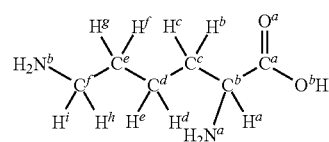

I

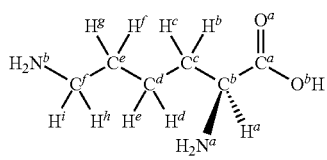

I-A or a salt or derivative thereof,
wherein
each $H^a$, $H^b$, $H^c$, $H^d$, $H^e$, $H^f$, $H^g$, $H^h$, and $H^i$ is independently $^1H$ or $2H$;
each $C^a$, $C^b$, $C^c$, $C^d$, $C^e$ and $C^f$ is independently $^{12}C$ or $^{13}C$; and at least two of $C^a$, $C^b$, $C^c$, $C^d$, $C^e$ and $C^f$ are $^{13}C$;
each $N^a$ and $N^b$ is independently $^{14}N$ or $^{15}N$;
$O^a$ and $O^b$ are both $^{16}O$ or $^{18}O$; and
wherein
each of the compounds has a gross mass difference relative to the mass of naturally occurring lysine;
the gross mass difference relative to lysine is the same for all of the compounds; and
the gross mass difference is an integer of 4 to 12;
with the provision that the compound is not:
2,3,3,4,4,5,5,6,6-$D_9$-L-lysine; 3,3,4,4,5,5,6,6-$D_8$-L-lysine; 1,2,3,4,5,6-$^{13}C_6$-L-lysine; 1,2,3,4,5,6-$^{13}C_6$,$^{15}N_2$-L-lysine; 4,4,5,5-$D_4$-L-lysine or 1,2-$^{13}C_2$-L-lysine.

In some embodiments of the composition, the gross mass difference is an integer of 4 to 14. In some embodiments of the composition, the gross mass difference is an integer of 6 to 12. In some embodiments, the gross mass difference is 4, 5, 6, 7, 8, 9, 10, 11, 12, 13, 14, 15 or 16. In some embodiments, the gross mass difference is 6. In some embodiments, the gross mass difference is 8. In some embodiments, the gross mass difference is 12. In some embodiments, the composition further comprises a lysine isotopologue that is not of Formula I or I-A, but which has a gross mass difference relative to naturally occurring lysine that is the same as the gross mass difference of the two or more different compounds of Formula I or I-A relative to naturally occurring lysine, and wherein the gross mass difference is an integer between 6 and 12.

In some embodiments of the composition, the two or more different compounds are selected from the group consisting of

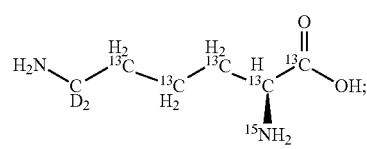

II

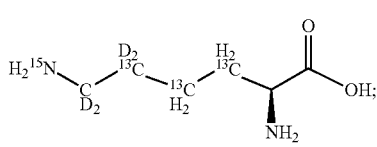

III

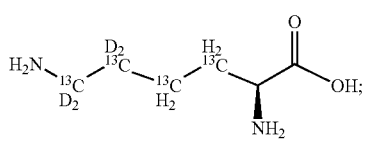

IV

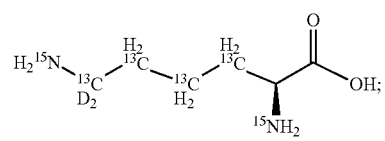

V and salts or derivatives thereof.

In some embodiments, the composition further comprises a lysine compound, wherein the lysine compound is not of Formula I or I-A. In some embodiments, the composition further comprises food for a mouse.

Polypeptides

In another aspect, a polypeptide is provided, where the polypeptide comprises any of the lysine isotopologues described herein. Thus, in some embodiments, the polypeptide has the lysine isotopologues incorporated into the peptide backbone of the polypeptide.

While the "polypeptides" described herein encompass both proteins and peptides, the description, for simplicity, will refer only to polypeptides. The discussion therefore also applies to both peptides and proteins, even when the term polypeptide is used. It is understood that the term "polypeptide" as used herein, refers to any polypeptide chain, containing one or more lysine isotopologues described herein, of three or greater amino acids, or, for example, of any length.

Isotopic substitution in a protein usually is accomplished by growing a bacterium or yeast, transformed by genetic engineering to produce the protein of choice, in a growth medium containing the lysine isotopologues described herein. Many such growth media are now commercially available. See, e.g., U.S. Pat. No. 5,324,658. Techniques for producing isotopically labeled proteins and other macromolecules, in mammalian or insect cells have also been described and can readily be adapted for use with the lysine isotopologues described herein. See U.S. Pat. Nos. 5,393,669 and 5,627,044; Weller, Biochemistry 35:8815-23, 1996; Lustbader, J. Biomol. NMR 7:295-304, 1996.

In further embodiments, the invention provides media capable of supporting the growth of cells in culture which comprises the lysine isotopologues described herein.

In yet further embodiments, the invention provides methods of producing an isotopically labeled peptide molecule which comprise providing a medium having the lysine isotopologues described herein, as described above; providing a cell culture that expresses the peptide molecule; growing the cell culture in the medium having the lysine isotopologues described herein under protein-producing conditions such that the cell expresses the peptide molecule in isotopically labeled form; and isolating the isotopically labeled peptide molecule from the medium.

The compositions and methods described herein therefore advantageously may be employed in connection with polypeptides that comprise the lysine isotopologues described herein, and have molecular masses of about 5 kD, 50 kD, 500 kD, 5,000 kD, 50,000 kD or more.

Polypeptides containing the specifically labeled amino acids may be chemically synthesized from scratch or expressed by cells in culture, for example by bacterial, yeast, mammalian or insect cells.

Edible Compositions

In another aspect, an edible composition is provided, where the edible composition comprises any of the compounds described herein or any of the compositions described herein.

In another aspect, an edible composition is provided, where the edible composition comprises any of the compounds or compositions described herein. In another aspect, an edible composition is provided, where the edible composition comprises any of the polypeptides described herein.

In some embodiments, the edible composition is an animal feed. In some embodiments, the animal is a mouse. In some embodiments, the edible composition contains lysine and/or a lysine derivative, wherein less than 1 wt % of the lysine and/or the lysine derivative has an isotopic abundance that is naturally occurring.

In some embodiments, the edible composition is a food for mice, i.e., mouse "chow." As such, the edible composition having stable isotope labeled lysine compounds, or compositions comprising the same, is food for an animal or rodent, such as mouse. The edible compositions described herein can be fed to a mouse. The mouse can then be sacrificed and the extent can be determined to which the stable isotope labeled lysine compounds have been incorporated into the mouse.

In some embodiments, the edible composition may include one or more lysine isotopologues of Formula I of the invention, in addition to one or more additional lysine isotopologues that are outside the scope of Formula I, where the isotopologues of Formula I and the isotopologues that are outside the scope of Formula I have the same gross mass difference (e.g., 4, 6, 8 or 12) relative to naturally occurring lysine.

Kits

In another aspect, a kit is provided, where the kit comprises any of the compounds described herein. In another aspect, a kit is provided, where the kit comprises any of the compositions described herein. In another aspect, a kit is provided, where the kit comprises any of the edible compositions described herein.

In some embodiments, any of the kits further comprises a control diet and the control diet comprises protein that has a naturally occurring isotopic abundance.

In some embodiments, the kit further comprises cell growth media, dialyzed fetal bovine serum, isotopically labeled amino acids other than lysine, instructions for use, solvents, supports and combinations thereof.

In some embodiments of the kit, the cell growth media has less than 1 wt % Lysine. In some embodiments of the kit, the cell growth media has less than 1 wt % arginine.

A Mouse Having the Lysine Isotopologue of Formula I Incorporated Therein

In another aspect, a mouse is provided, wherein the mouse comprises lysine, and wherein between 1% and 99% of the lysine derives from the lysine isotopologue of Formula I or I-A. In some embodiments, the mouse has between 1% and 25% or 25% and 50% or between 50% and 99% lysine which is the lysine isotopologue of Formula I or I-A. For example, the mouse may be fed a diet comprising the lysine isotopologue compounds of Formula I or I-A, or compositions or edible compositions comprising the same, for a period of 2 weeks, 4 weeks, 2 months, 4 months, 1 year or 2 years.

The mice described herein, which are fed the lysine isotopologue compounds of Formula I or I-A, or the compositions or edible compositions comprising the same, for a period of 2 weeks, 4 weeks, 2 months, 4 months, 1 year or 2 years, may be subjected to perturbation, by, for example, treatment with a drug or other species or condition that modifies biological function and changes in protein concentration in blood or organs, which may be identified.

Syntheses

Also provided are methods of producing a stable isotope labeled lysine compound. In addition, it should be appreciated that stable isotope labeled lysine compounds described herein may be produced according to other known synthetic procedures, wherein a standard reactant in the synthesis is replaced with a corresponding isotopically labeled reactant. Various protecting groups, deprotections and substitutions may be used to improve efficiency, yield, cost and like considerations.

In one aspect, a process is provided for the synthesis of site specific labeled L-lysine isotopologues labeled with carbon-13 and/or nitrogen-15 and/or deuterium.

In one embodiment, the compounds described herein are prepared from synthetic route that is based on a synthesis of L-glutamic acid, followed by conversion to L-lysine by chain extension with cyanide. N-tBOC-L-glutamic acid 1-t-butyl ester is the first intermediate. This may be synthesized, for example, via the route shown in Scheme 1 below.

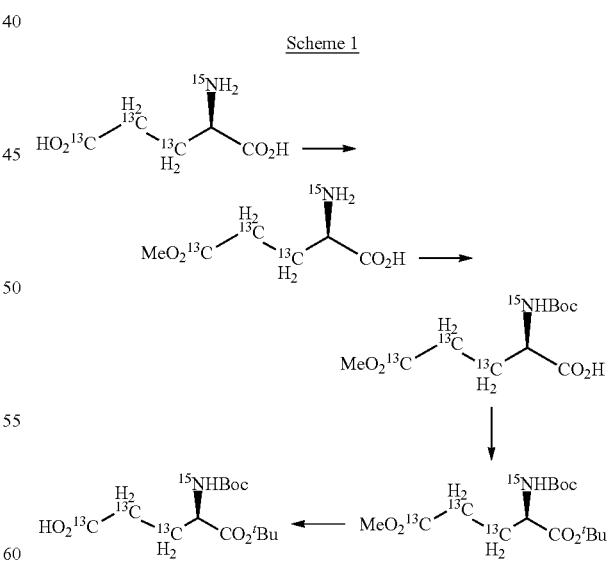

Scheme 1

This route may, under certain conditions, lead to partial racemization of the L-glutamic acid, which can be ameliorated later in the synthesis. Consequently, an alternative route has also been used that avoids racemization as shown in Scheme 2 below.

Scheme 2

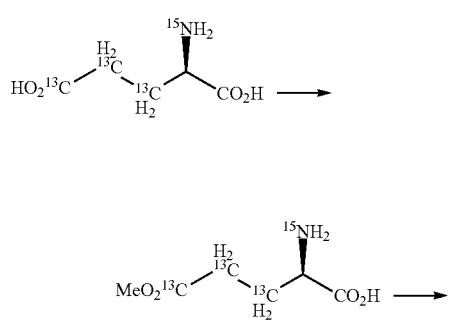

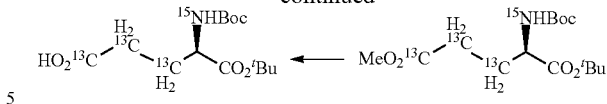

In some embodiments, selection of the protecting groups (BOC and t-butyl ester) shown in these schemes is important for the success of the synthesis, because other protecting groups (such as CBZ and benzyl ester) may interfere with the subsequent steps and thus lower yields and the extent of deuterium enrichment.

In another embodiment, the route to L-lysine from the protected amino acid is shown in Scheme 4 below.

Scheme 4

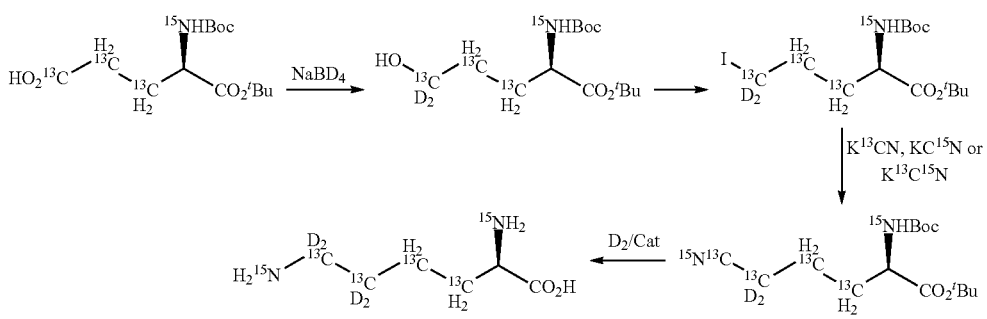

-continued

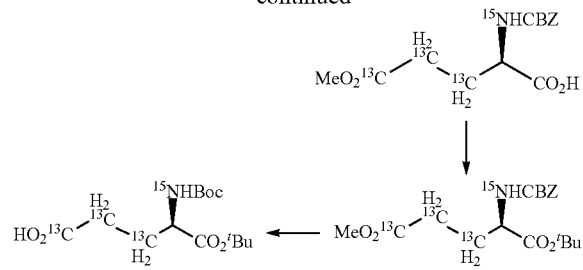

A third alternative route shown in Scheme 3 reverses the steps and also avoids racemization of the L-glutamic acid.

Scheme 3

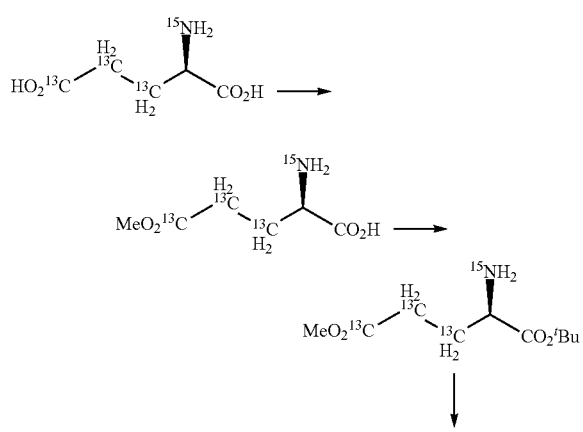

In another embodiment, the synthesis of the site-specifically labeled L-glutamic acid is based on the preparation of α-ketoglutaric acid from diethyl succinate and diethyl oxalate followed by enzymatic reductive amination, as shown in Scheme 5 below.

Scheme 5

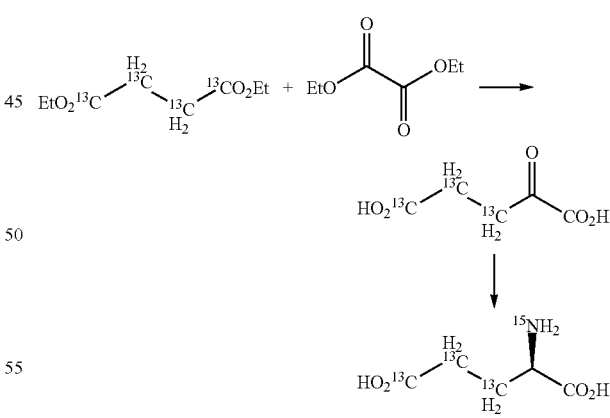

In some embodiments, when the diethyl oxalate is labeled with $^{13}C$ and the diethyl succinate is unlabeled, the resulting glutamic acid is 1,2-$^{13}C_2$, in place of the 3,4,5-$^{13}C_3$ labeling pattern as shown. Similarly either $^{15}N$ or $^{14}N$ can be incorporated into the compounds described herein depending on the nature of the ammonium hydroxide used in the procedure.

As known to the skilled artisan, alternative syntheses are available in the literature to prepare glutamic acid from α-ketoglutaric acid using chemical means and giving a racemic product. The racemate is then resolved by preparation of an N-acetyl derivative and enzymatic hydrolysis.

The synthetic methods described above can be used to prepare the compounds described herein. In one aspect, for example, a process is provided for preparing a compound of Formula I or I-A:

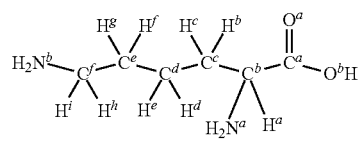

I

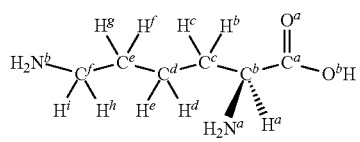

I-A or a salt or derivative thereof, said process comprising one or more steps selected from the group of steps (a)-(i) consisting of:

(a) deprotecting a compound of Formula 10 to form a compound of Formula 11a;

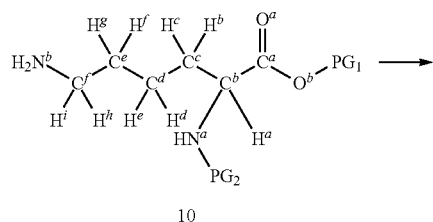

10

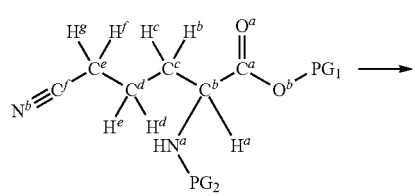

11a (b) reducing a compound of Formula 9 to form a compound of Formula 10;

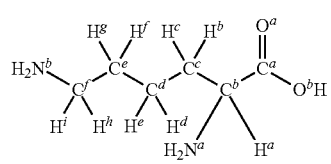

9

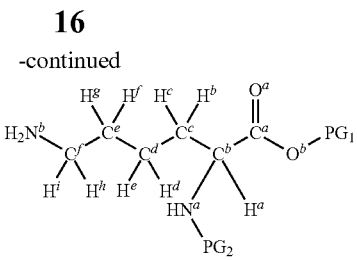

10

(c) contacting a compound of Formula 8 with a —CN salt to form a compound of

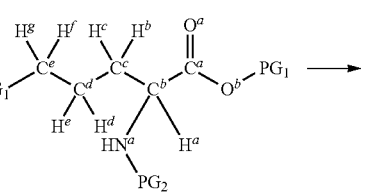

8

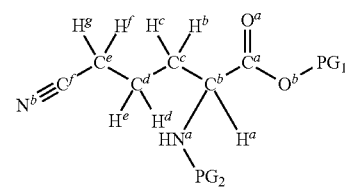

9

(d) contacting a compound of Formula 7 with a reagent to form a compound of Formula 8, wherein the reagent comprises a leaving group;

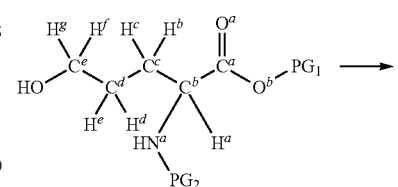

7

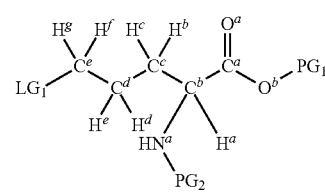

8

(e) reducing a compound of Formula 6 to form a compound of Formula 7;

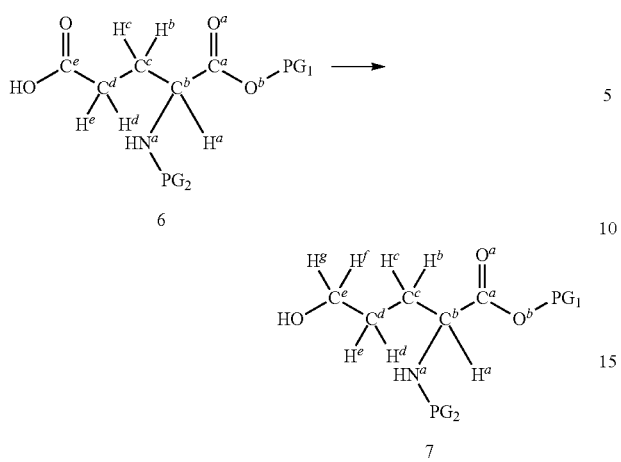

6

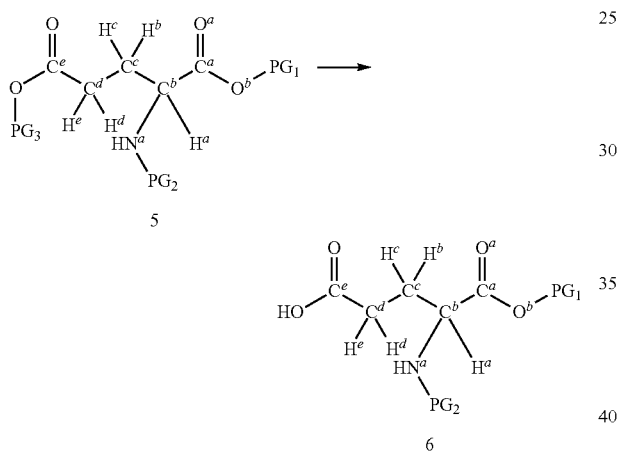

7

(f) protecting a compound of Formula 5 to form a compound of Formula 6;

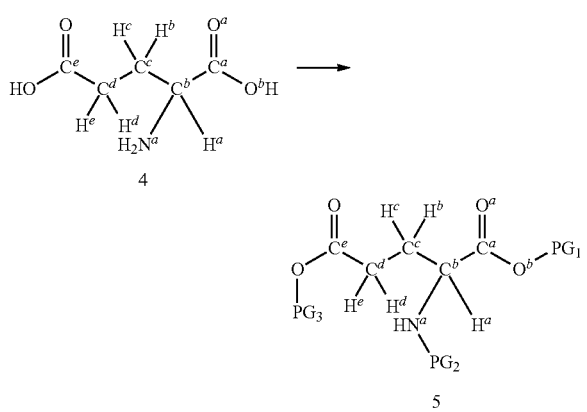

5

↓

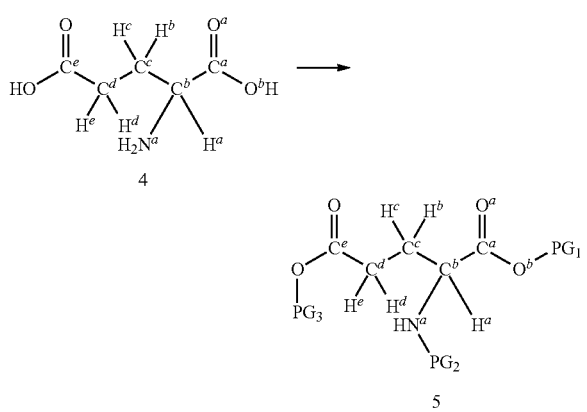

6

(g) protecting a compound of Formula 4 to form a compound of Formula 5;

4

↓

5

(h) contacting a compound of Formula 3 with an ammonium salt to form a compound of Formula 5; of Formula 4; and

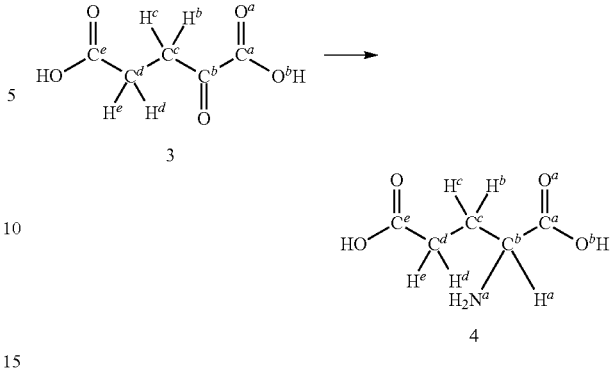

3

↓

4

(i) contacting a compound of Formula 1 with the compound of Formula 2 to form a compound of Formula 3;

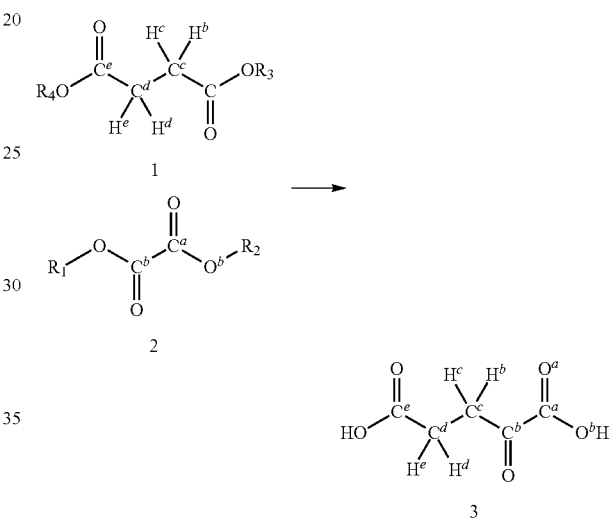

1

2

↓

3 or a salt or derivative thereof,
wherein
each $H^a$, $H^b$, $H^c$, $H^d$, $H^e$, $H^f$, $H^g$, $H^h$, and $H^i$ is independently $^1H$ or $^2H$;
each $C^a$, $C^b$, $C^c$, $C^d$, $C^e$ and $C^f$ is independently $^{12}C$ or $^{13}C$; and at least two of $C^a$, $C^b$, $C^c$, $C^d$, $C^e$ and $C^f$ are $^{13}C$;
each $N^a$ and $N^b$ is independently $^{14}N$ or $^{15}N$;
$O^a$ and $O^b$ are both $^{16}O$ or $^{18}O$;
each $R^1$, $R^2$, $R^3$ and $R^4$ is independently hydrogen or $C_1$-$C_6$ alkyl;
each $PG^1$ and $PG^3$ is independently a carboxylic acid protecting group;
each $PG^2$ is independently an amino protecting group; and
$LG^1$ is a leaving group.

In some embodiments, the process comprises two of steps (a)-(i). In some embodiments, the process comprises three of steps (a)-(i). In some embodiments, the process comprises four of steps (a)-(i). In some embodiments, the process comprises five of steps (a)-(i). In some embodiments, the process comprises six of steps (a)-(i). In some embodiments, the process comprises seven of steps (a)-(i). In some embodiments, the process comprises eight of steps (a)-(i). In some embodiments, the process comprises all steps (a)-(i).

In some embodiments of the process, $LG^1$ is iodo. In some embodiments of the process, $PG^1$ is iodo. In some embodiments, the process further comprises contacting the compound of Formula 7 with an enzyme that catalyzes the rate of formation of the compound of Formula 9.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

SYNTHETIC EXAMPLES

Example 1: Preparation of α-ketoglutaric acid

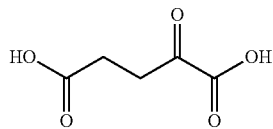

A 5 liter round bottom flask was charged with potassium ethoxide and diethyl ether (800 ml). To this was added diethyl oxalate in diethyl ether (100 ml) (229.6 g, 1.573 mol) in diethyl ether (100 ml) with stirring. Diethyl succinate (280 g, 1.573 mol) was added in a single portion. The mixture was allowed to stand for 30 minutes. Water (925 ml) was added and the reaction mixture transferred to a separatory funnel. The organic layer was removed and the aqueous layer extracted with diethyl ether. The combined organic layers were extracted with water and set aside. The combined aqueous layers were acidified with concentrated hydrochloric acid (167 ml) and the product extracted into diethyl ether. The ethereal solution was dried over sodium sulfate and concentrated to a thick orange oil which was transferred to a 3 liter flask and treated with concentrated hydrochloric acid (1000 ml) at room temperature overnight. The mixture was then heated to reflux with stirring and maintained at reflux until evolution of gas ceased. The mixture was then transferred to a rotary evaporator and co-evaporated with water (100 ml) six times. The mixture was then concentrated to dryness and dried under high vacuum at 40° C. for 6 hours. Yield of 3,4,5-$^{13}C_3$-α-ketoglutaric acid: 196 g at 85% chemical purity (83%). Chemical purity measured by HPLC (Rezex® ion exchange column, 0.1% TFA in water, 0.6 ml/min, UV @215 nm) against authentic standard (retention times identical). KF (water content): 17.5%. M/z (methylated derivative): 192 ($M^+$-OMe). $^1$H NMR (300 MHz, $D_2O$/TMSP, ppm) 2.3 (2H, m); 2.7 (2H, m). $^{13}C$ NMR (75 MHz, $D_2O$/TMSP, ppm) 28.07 (m); 32.3 (m); 176.9 (m)

Unlabeled diethyl succinate combined with $^{13}C_2$-diethyl oxalate gives 1,2-$^{13}C_2$-α-ketoglutaric acid, combining $^{13}C_4$-diethyl succinate with $^{13}C_2$-diethyl oxalate gives 1,2,3,4,5-α-ketoglutaric acid.

Example 2: Preparation of L-glutamic acid

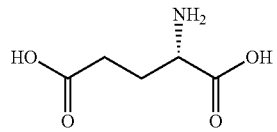

A 12 liter round bottom flask was charged with potassium phosphate buffer (4.2 L, from a stock solution prepared from 18 L water, 1.6 L 1M $K_2HPO_4$ and 0.4 L 1 M $KH_2PO_4$ at pH 7.4), and 3,4,5-$^{13}C_3$ α-ketoglutaric acid (77 g, 85% pure, 0.44 mol). The pH of the resulting solution was adjusted to 7.4 by the addition of 6M KOH solution (192 ml). To this solution was added $^{15}N$-ammonium chloride (34.7 g, 0.64 mol) and glucose-6-phosphate disodium salt (127.1 g, 0.42 mol). The pH of the solution was adjusted to 7.4 by addition of 6M KOH solution (28 ml). Adenosine diphosphate sodium salt (1.8 g, 4 mmol) and 13-NADP sodium salt (0.4 g, 0.5 mmol) were added and the solution adjusted to pH 7.6 with 6 M KOH (5 ml). The solution was diluted with 2.48 L potassium phosphate buffer and glutamate dehydrogenase (25 k units) and glucose-6-phosphate dehydrogenase (2.5 k units) added. The reaction mixture was warmed to 45° C. After five days glutamate dehydrogenase (5 k units) and glucose-6-phosphate dehydrogenase (0.5 k units) were added after adjusting pH to 7.6 with 6 M KOH (80 ml). After a further 24 h the reaction mixture was allowed to cool and the pH adjusted to 4.8 with glacial acetic acid (120 ml). The mixture was stirred for 30 minutes and charcoal (15 g) added. After stirring the mixture for 2 hours the solution was filtered through a glass fibre filter and added to the top of a AG50 ($H^+$ form) resin column, formed from 3 L resin. The column was rinsed with 16 L of deionized water and the glutamic acid eluted with 1M ammonium hydroxide solution. The ninhydrin positive fractions were combined and treated with charcoal (10 g), filtered and retreated with charcoal (7 g) and refiltered after stirring overnight. The solution was filtered through a 0.2 m polyethylene filter and concentrated under reduced pressure on a rotary evaporator. The concentrated solution was treated to 6M hydrochloric acid to pH 3.1 and chilled to 4° C. for 48 hours. The resulting crystalline glutamic acid was collected at the pump and dried under vacuum at 45° C. Yield of 3,4,5-$^{13}C_3$,$^{15}N$-L-glutamic acid: 52.7 g (80%). Analytical data: Chemical purity: 99.8% by HPLC. M/z: 257 (N-trifluoroacetyl, O-ethyl ester derivative —F). $^1$H NMR (300 MHz, $D_2O$/TMSP, ppm) 2.5 (1H, m); 2.1 (2H, m); 2.4 (1H, m); 3.2 (m, 1H). $^{13}C$ NMR (75 MHz, $D_2O$/TMSP, ppm) 31.7 (m); 34.1 (m); 182.9 (m)

The stereospecific addition of ammonia occurs in an enzyme catalyzed step. Alternatives are available in the literature but are more complex.

By varying the isotopomers used in the above procedure, other site specifically labeled glutamic acids may be prepared:

3,4,5-$^{13}C_3$-L-glutamic acid 3,4,5-$^{13}C_3$, $^{15}N$-L-glutamic acid 1,2-$^{13}C_2$-L-glutamic acid 1,2-$^{13}C_2$, $^{15}N$-L-glutamic acid

Example 3: Preparation of L-glutamic acid 5-methyl ester

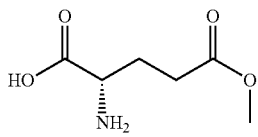

Method A

Glutamic acid (55 g; 0.36 mol) was suspended in 150 mL of H$_2$O and mixture cooled to 0° C. To the obtained slurry, was added concentrated hydrochloric acid (42.5 g, 0.43 mol, 1.2 Eq.) dropwise via dropping funnel while the temperature is maintained around 10° C. The solution became homogeneous and stirring was continued for an additional 15 min.

The water was then removed under vacuum and residual hydrochloric acid was chased by re-dissolving the solid in 150 mL of water and removing the water. This operation was done twice and the Glutamic acid hydrochloride salt was dried in oven at 45° C. overnight.

To the bone dry Glutamic acid hydrochloride was added a catalytic amount (~175 L) of concentrated hydrochloric acid and 2 L of anhydrous Methanol. The resulting homogeneous solution was allowed to stir at room temperature for 7 to 8 days. $^1$H and $^{13}$C NMR samples shows that the esterification is complete and about 3% of bis dimethyl ester was formed. Methanol was removed and the resulting solid was dried overnight at 40° C. in vacuum. The product was used without further purification.

Method B

Glutamic acid (22.1 g, 0.15 mol) was suspended in methanol (450 mL), under nitrogen at room temperature. TMS chloride (35.9 g, 0.33 mol) was then added dropwise over 5 minutes (note: by the end of addition most of solids dissolved). The mixture was stirred for additional 5 min and tested by TLC (15% ammonia in methanol, ninhydrin visualization)—traces of starting material and no bis-methyl ester were visible on TLC. The mixture was stirred for additional 5 min, concentrated on a roto-vap and then dried in a vacuum oven (40° C.) to give pure by TLC and NMR product as a white solid. Yield: 30.0 g (100%). $^1$H NMR (300 MHz, CD$_3$OD, ppm) 2.2 (2H, m), 2.6 (2H, m), 3.7 (3H, s), 4.1 (1H, t) $^{13}$C NMR (75 MHz, CD$_3$OD, ppm) 26.6, 30.4, 52.5, 53.2, 171.4, 174.3.

1,2,3,4,5-$^{13}$C$_5$, $^{15}$N-L-Glutamic acid (59.8 g, 0.39 mol) was suspended in dry methanol (1,170 ml) at room temperature. TMS chloride (93.3 g, 0.90 mol) was added over 5 minutes. After a further 5 minutes, TLC (methanol, ethanol, ammonium hydroxide; 4.5:4.5:1) showed completion. The mixture was concentrated to dryness on a rotary evaporator and dried under high vacuum overnight. Yield 1,2,3,4,5-$^{13}$C$_5$, $^{15}$N-L-glutamic acid, 5-methyl ester: 65.2 g (quant). Used directly in the next step.

Example 4: Preparation of L-glutamic acid, N-t-butoxycarbonyl, 5-methyl ester

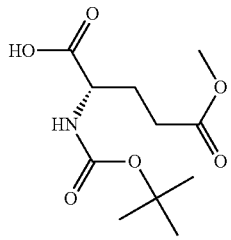

Glutamic acid 5-methyl ester (20.0 g, 0.101 mol) was dissolved in 375 mL of dioxane/water (2:1) at 0° C. Boc$_2$O (26.5 g, 0.121 mol) was then added followed by solid NaHCO$_3$ (21.3 g, 0.253 mol). The mixture was stirred at 0° C. for 2 hours and then at room temperature overnight. TLC (15% ammonia in methanol, ninhydrin visualization) showed only traces of starting material present in the mixture. Solvents were removed on a rotary evaporator, and the semisolid residue was resuspended in 10% NaHCO$_3$ (300 mL). The mixture was extracted with ether (3×100 mL) and acidified with solid citric acid (approx 65 g, 0.3 mol) to pH 4. The resulting mixture was extracted with AcOEt (3×100 mL). Combined acetate extracts were washed with brine (100 mL), dried over MgSO$_4$, filtered and concentrated on a rotary evaporator to give pure by NMR product as a colorless oil which solidified upon standing. Yield: 23.7 g (90%). $^1$H NMR (300 MHz, CDCl$_3$, ppm) 1.4 (9H, s, 1.9 (1H, m), 2.2 (1H, m), 2.4 (2H, m), 3.6 (3H s), 4.25 (1H, m), 5.2 (0.5H, bs), 6.8 (0.5H, bs), 11.5 (1H, bs). $^{13}$C NMR (75 MHz, CDCl$_3$, ppm) 27.5, 27.6, 28.3, 29.7, 30.1, 51.9, 52.7, 53.7, 80.3, 82.1, 155.7, 156.9, 173.2, 173.5, 175.6, 176.2

1,2,3,4,5-$^{13}$C$_5$, $^{15}$N-L-glutamic acid, 5-methyl ester (65.2 g, 0.39 mol) was dissolved in dioxane/water (1500 ml, 2:1) at 0° C. Boc anhydride (102.14 g, 0.47 mol) was added followed by sodium bicarbonate (81.9 g, 0.92 mol) and the resulting mixture stirred at 0° C. for 2 hour and at room temperature overnight. The reaction mixture was then concentrated under reduced pressure and suspended in aqueous sodium bicarbonate (10%, 1 L) and washed with diethyl ether. The aqueous phase was mixed with ethyl acetate and acidified with citric acid to pH 4. The product was extracted into ethyl acetate, dried over magnesium sulfate and concentrated to dryness under reduced pressure. Yield of 1,2,3,4,5-$^{13}$C$_5$, $^{15}$N-L-glutamic acid, N-t-butoxycarbonyl, 5-methyl ester: 101.5 g (97%). $^1$H NMR (300 MHz, CDCl$_3$, ppm) 1.49 (9H, s), 1.7-2.8 (4H, m), 3.69 (3H, s), 4.39 (1H, d of m), 5.20 (1H, d of d). $^{13}$C NMR (75 MHz, CDCl$_3$, ppm) 29 (t), 31 (m), 54 (m), 172 (d), 178 (d).

Used directly in the next step.

Example 5: Preparation of L-glutamic acid, N-t-butoxycarbonyl, 1-t-butyl ester, 5-methyl ester

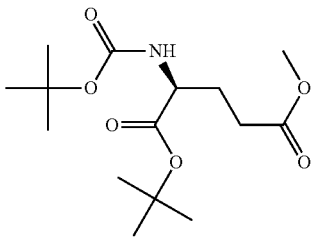 [SMILES: COC(=O)CC[C@H](NC(=O)OC(C)(C)C)C(=O)OC(C)(C)C]

Solution of N-Boc-Glutamic acid 5-methyl ester (23.5 g, 0.09 mol) in dichloromethane (50 mL) was added under nitrogen, dropwise over 40 minutes to a solution of DCC (22.3 g, 0.108 mol), DMAP (1.08 g, 10 mol %), and tert-butyl alcohol (66.7 g, 0.9 mol) in dichloromethane (450 mL) at 0° C. After all acid was added, the mixture was stirred under nitrogen at 0° C. for additional hour. TLC (hexanes/ethyl acetate 7:3, KMnO$_4$ visualization) after this time showed absence of starting material. The mixture was allowed to warm up to room temperature and stirred overnight. Reaction mixture was filtered from solids and concentrated on a roto-vap. Cloudy, containing small amount of solid colorless oil was dissolved in ether (300 mL), washed with 10% citric acid solution (2×50 mL), saturated NaHCO$_3$ (2×50 mL) and brine (50 mL), dried over MgSO$_4$, filtered, and concentrated in vacuo to give 31.3 g (110%) of a colorless oil. NMR indicates presence of DCC (approx 10%). Material was used in the subsequent step without additional purification. $^1$H NMR (300 MHz, CDCl$_3$, ppm) 1.3 (9H, s), 1.4 (9H, s), 1.9 (1H, m), 2.2 (1H, m), 2.4 (2H, m), 3.6 (3H, s), 4.2 (1H, m), 5.1 (1H, m).

$^{13}$C NMR (75 MHz, CDCl$_3$, ppm) 28.0, 28.3, 30.1, 34.9, 51.7, 53.3, 55.7, 80.3, 82.1, 171.3, 173.3.

1,2,3,4,5-$^{13}$C$_5$, $^5$N-L-glutamic acid, N-t-butoxycarbonyl, 5-methyl ester (101.5 g, 0.38 mol) was dissolved in dichloromethane at 0° C. and added dropwise to a solution of DCC (96.6 g, 0.468 mol), DMAP (4.68 g, 0.05 mol) and t-butanol (289 ml, 3.90 mol) in dichloromethane (2 L). The reaction mixture was stirred for 1 h at 0° C. and allowed to warm to room temperature overnight. The mixture was then filtered and concentrated under reduced pressure. The residue was dissolved in diethyl ether (1200 ml) and washed with aqueous citric acid (10%), saturated sodium bicarbonate, brine and dried over magnesium sulfate. The solution was then filtered and concentrated under reduced pressure. Yield of 1,2,3,4,5-$^{13}$C$_5$, $^{15}$N-L-glutamic acid, N-t-butoxycarbonyl, 1-t-butyl ester, 5-methyl ester: 104.9 g (85%). TLC (20% ethyl acetate/hexane) showed a single spot. $^1$H NMR (300 MHz, CDCl$_3$, ppm) 1.42 (9H, s), 1.47 (9H, s), 1.7-2.7 (4H, m), 3.72 (3H, s), 4.21 (1H, d of m), 5.18 (1H, d of d). $^{13}$C NMR (75 MHz, CDCl$_3$, ppm) 28 (t), 31 (m), 53 (m), 172 (d), 175 (d).

Used directly in the next step.

Example 6: Preparation of L-glutamic acid, N-t-butoxycarbonyl, 1-t-butyl ester

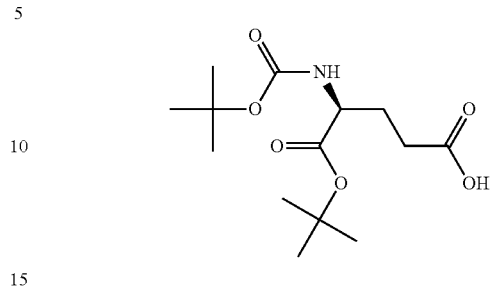

Solution of crude N-Boc-Glutamic acid 1-tert-butyl ester, 5-methyl ester from the previous step (30.4 g, 95.8 mmol) in THF (300 mL) was mixed with 144 mL of 1N LiOH. After 40 minutes of stirring, TLC showed absence of starting material. THF was removed on a roto-vap. Aqueous solution was extracted with AcOEt (3×100 mL) and acidified to pH 4 with solid citric acid. The mixture was extracted again with AcOEt (3×100 mL). Acetate extracts from acidic extraction were combined, washed with brine (2×50 mL), dried (MgSO$_4$), and concentrated on a roto-vap to give product as a colorless oil. Yield: 25 g (92% based on Boc-Glu(OMe)-OH). $^1$H NMR (300 MHz, CDCl$_3$, ppm) 1.3 (9H, s), 1.4 (9H, s), 1.9 (1H, m), 2.2 (1H, m), 2.4 (2H, m), 4.2 (1H, m), 5.1 (1H, m), 10.3 (1H, bs), $^{13}$C NMR (75 MHz, CDCl$_3$, ppm) 28.0, 28.3, 30.2, 53.3, 80.1, 82.4, 155.6, 171.4, 178.2

1,2,3,4,5-$^{13}$C$_5$, $^{15}$N-L-glutamic acid, N-t-butoxycarbonyl, 1-t-butyl ester, 5-methyl ester (104.9 g, 0.32 mol) was dissolved in THF (1 L) and lithium hydroxide solution (1M, 500 ml) was added. The mixture was stirred for 40 minutes at room temperature, whereupon TLC (20% ethyl acetate/hexane) showed no remaining starting material. The mixture was concentrated to remove THF and then extracted with ethyl acetate. The aqueous layer was acidified with citric acid to pH 4 and extracted with ethyl acetate. The latter ethyl acetate extracts were combined, washed with brine, dried over magnesium sulfate and concentrated to dryness to give 1,2,3,4,5-$^{13}$C$_5$, $^{15}$N-L-glutamic acid, N-t-butoxycarbonyl, 1-t-butyl ester: 84.6 g (82%). Chemical purity estimated by 1H NMR>98%. $^1$H NMR (300 MHz, CDCl$_3$, ppm) 1.45 (9H, s), 1.48 (9H, s), 1.65-2.75 (4H, m), 3.69 (3H, s), 4.21 (1H, d of m), 5.21 (1H, d of d). $^{13}$C NMR (75 MHz, CDCl$_3$, ppm) 29 (t), 31 (m), 54 (m), 172 (d), 178 (d). Chiral purity (HPLC, Marfeys reagent): >90% L)

Example 7: Preparation of L-glutamic acid, N-carbobenzyloxy, 1-t-butyl ester, 5-methyl ester

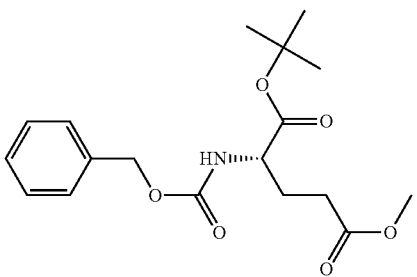 [SMILES: COC(=O)CC[C@H](NC(=O)OCc1ccccc1)C(=O)OC(C)(C)C]

L-Glutamic acid, N-carbobenzyloxy, 5-methyl ester (2.5 g, 8.5 mmol), dichloromethane (20 ml) and sulfuric acid (concentrated, 85 µl) were placed in a Schlenk tube equipped with a magnetic stirrer. The Schlenk tube was cooled to −78° C. and 15-20 ml of isobutylene condensed into the mixture. The reaction was allowed to warm to −10° C. and the tube sealed. The reaction was then allowed to warm to room temperature and stirred for 65 hours. The reaction mixture was then neutralized with aqueous sodium bicarbonate and the isobutylene allowed to evaporate. The layers were allowed to separate and the aqueous phase extracted with dichloromethane. The combined organic phases were washed with water and concentrated under reduced pressure. Yield of L-glutamic acid, N-carbobenzyloxy, 1-t-butyl ester, 5-methyl ester 2.6 g (85%). $^1$H NMR (300 MHz, CDCl$_3$, ppm) 1.4 (9H, s); 2.0 (1H, m); 2.2 (1H, m); 1.4 (2H, m); 3.7 (3H, s); 4.3 (1H, m); 5.1 (2H, m); 5.4 (1H, bs); 7.4 (5H, arom., s).

Example 8: Preparation of L-glutamic acid, N-t-butoxycarbonyl, 1-t-butyl ester, 5-methyl ester (from 7)

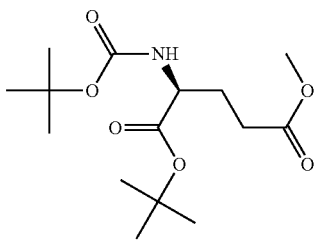 [SMILES: COC(=O)CC[C@H](NC(=O)OC(C)(C)C)C(=O)OC(C)(C)C]

A Parr bottle was charged with L-glutamic acid, N-carbobenzyloxy, 1-t-butyl ester, 5-methyl ester (1.3 g, 3.7 mmol) in methanol (30 ml) and a catalytic amount of Pd/C (10%). BOC anhydride (0.89 g, 4.07 mmol) and the mixture was hydrogenated at 60 psi for 4 hours. The production was filtered and concentrated to give an oil. Yield of L-glutamic acid, N-t-butoxycarbonyl, 1-t-butyl ester, 5-methyl ester: 1.1 g (94%). $^1$H NMR (300 Mz, CDCl$_3$, ppm) 1.4 (9H, s); 1.5 (9H, s); 1.9 (1H, m); 1.2 (1H, m); 2.4 (2H, m); 3.7 (3H, s); 4.2 (1H, m); 5.1 (1H, bs).

Example 9: Preparation of L-glutamic acid, N-t-butoxycarbonyl, 1-t-butyl ester (via L-glutamic acid, 1-t-butyl ester, 5-methyl ester)

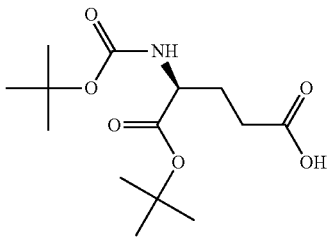 [SMILES: CC(C)(C)OC(=O)N[C@@H](CCC(=O)O)C(=O)OC(C)(C)C]

L-Glutamic acid 5-methyl ester (2.5 g, 15.5 mmol) was added to a solution of perchloric acid (70%, 1.5 ml) in t-butyl acetate (100 ml). The mixture stirred at room temperature for 3 hours. The reaction mixture was then extracted with phosphate buffer (pH 3) and the aqueous layer washed with diethyl ether. The combined aqueous layers were adjusted to pH 8 with sodium carbonate and the product extracted into ethyl acetate. The organic layers were washed with brine and dried over magnesium sulfate. The organic layer was filtered, concentrated to approximately 50 ml and treated with BOC anhydride ((5.07 g, 23.3 mmol) and sodium bicarbonate (5.0 g, 60 mmol). The reaction mixture was stirred overnight at room temperature and then treated with aqueous sodium bicarbonate. The ethyl acetate layer was separated, dried over magnesium sulfate, filtered and concentration to give an oil (5 g, quant). The oil was purified by column chromatography (silica, gradient ethyl acetate/hexane, 10%→20%) to give L-glutamic acid, 1-t-butyl ester, 5-methyl ester 5 g (100%). This material was taken up in THF (50 ml) and treated with aqueous lithium hydroxide (1M, 25 ml) and stirred at room temperature for 40 minutes. The aqueous layer was washed with ethyl acetate and the organic layer discarded. Ethyl acetate was added to the aqueous phase and the aqueous phase acidified to pH 4. The product was extracted into ethyl acetate and the combined organic phases washed with brine and evaporated to dryness under reduced pressure. Overall yield of L-glutamic acid N-t-butoxycarbonyl, 1-t-butyl ester 1.66 g (34% from 5-methyl ester)

Example 10: Preparation of (R)-2-(t-butoxycarbonylamino)-5-hydroxypentanoic acid, t-butyl ester

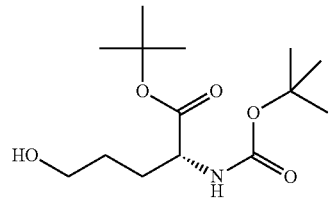 [SMILES: CC(C)(C)OC(=O)N[C@H](CCCO)C(=O)OC(C)(C)C]

Ethyl chloroformate (15.1 g, 139 mmol) in THF (480 ml) was added to a solution of 1,2,3,4,5-$^{13}$C$_5$, 2-$^{15}$N-L-glutamic acid N-t-butoxycarbonyl, 1-t-butyl ester (41.0 g, 135 mmol) and triethylamine (14.25 g, 140.9 mmol) in THF (480 ml) at −5° C. and the mixture allowed to stir at −5° C. for 1 hour. The solution was filtered and the resulting solution added dropwise to sodium borohydride (15.5 g, 0.41 mol) in water (105 ml) and THF (210 ml) at 0° C. and allowed to warm to room temperature overnight with stirring. The solution was then acidified to pH 3 and the product extracted into ethyl acetate. The organic layer was washed with sodium hydroxide (0.5M), brine and water. The organic layer was filtered through a pad of silica, dried and evaporated under reduced pressure. TLC (10% methanol/dichloromethane) showed a single product (R$_f$=0.6). Yield: 33.0 g (83%). $^1$H NMR (300 MHz, CDCl$_3$, ppm) 1.45 (9H, s), 1.50 (9H, s), 1.40-2.00 (4H, m), 2.04 (1H, s), 3.68 (2H, d of t), 4.25 (1H, d of m), 5.18 (1H, d of d). $^{13}$C NMR (75 MHz, CDCl$_3$, ppm) 28 (t), 30 (m), 53 (m), 62 (d), 172 (d).

Ethyl chloroformate (9.22 g, 85 mmol) in THF (130 ml) was added dropwise to a solution of L-glutamic acid N-t-butoxycarbonyl, 1-t-butyl ester (25 g, 82 mmol) in THF (130 ml) at −10° C. over 15 minutes. The mixture was stirred maintaining temperature between −10° C. and −5° C. for 1 hour. The mixture was filtered and the resulting solution added to a solution of sodium borodeuteride (10.5 g, 250 mmol) in D$_2$O (65 ml) and THF (130 ml) at 0° C. over 1 hour. The reaction mixture was allowed to warm to room temperature and was stirred overnight. The mixture was then neutralized to pH 7 with 3 M DCl and the bulk of the THF removed under reduced pressure. The aqueous residue was acidified with 3 M DCl to pH 4 and the product extracted into ethyl acetate. The combined organic layers were washed with saturated sodium bicarbonate and brine, dried over magnesium sulfate and concentrated under reduced pressure to give a colorless oil. Yield of 5,5-D$_2$-(R)-2-(t-butoxycarbonylamino)-5-hydroxypentanoic acid, t-butyl ester: 16.5 g (69%). $^1$H NMR (300 MHz, CDCl$_3$, ppm) 1.3 (9H, s), 1.4 (9H, s), 1.5 (3H, m), 1.8 (1H, m), 2.2 (1H, bs), 4.1 (1H, m), 5.1 (1H, m). $^{13}$C NMR (75 MHz, CDCl$_3$, ppm) 28.0, 28.3, 29.7, 53.6, 79.7, 81.9, 155.6, 171.9.262 (M$^+$-BOC).

Example 11: Preparation of (R)-2-(t-butoxycarbonylamino)-5-iodopentanoic acid, t-butyl ester

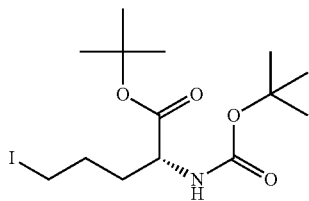 [SMILES: CC(C)(C)OC(=O)N[C@H](CCCI)C(=O)OC(C)(C)C]

Triphenylphosphine (58.6 g, 224 mmol) was dissolved in dichloromethane (675 ml) and cooled to 0° C. Iodine (56.8 g, 224 mmol) was added in portions. After 1 hour a mixture of 1,2,3,4,5-$^{13}$C$_5$, 2-$^{15}$N—(R)-2-(t-butoxycarbonylamino)-5-hydroxypentanoic acid, t-butyl ester (33.0 g, 112 mmol) and imidazole (15.63 g, 230 mmol) in dichloromethane (600 ml) was slowly added. The reaction mixture was stirred for 2 hours at 0° C. The reaction mixture was evaporated to dryness under reduced pressure and dissolved in diethyl ether. The suspension was filtered through a pad of silica and evaporated to dryness. Yield: 31.85 g (87%). $^1$H NMR (300 MHz, CDCl$_3$, ppm) 1.50 (9H, s), 1.55 (9H, s), 1.25-2.20 (4H, m), 2.04 (1H, s), 3.20 (2H, d of t), 4.21 (1H, d of m), 5.07 (1H, d of d). $^{13}$C NMR (75 MHz, CDCl$_3$, ppm) 6 (t), 29 (m), 33 (m), 53 (d), 172 (d).

Triphenylphosphine (27.9 g, 107 mmol) in dichloromethane (300 ml) was cooled to 0° C. and treated with iodine (27 g, 107 mmol). The mixture was stirred for 1 h at 0° C. and a solution of 5,5-D$_2$-(R)-2-(t-butoxycarbonylamino)-5-hydroxypentanoic acid, t-butyl ester (15.5 g, m 53.2 mmol) and imidazole (7.4 g, 109 mmol) in dichloromethane (160 ml) added dropwise maintaining the reaction temperature at 0° C. The mixture was stirred at 0° C. for a further hour and then concentrated under reduced pressure. The residue was taken up in diethyl ether, filtered and concentrated under reduced pressure. The product was treated with diethyl ether and hexanes to precipitate triphenylphosphine oxide. The final product was a clear, colorless oil. Yield of 5,5-D$_2$-(R)-2-(t-butoxycarbonylamino)-5-iodopentanoic acid, t-butyl ester (21.5 g, 80% pure, 80% yield). $^1$H NMR (300 MHz, CDCl$_3$, ppm) 1.4 (9H, s); 1.5 (9H, s); 1.6 (2H, m); 1.8 (2H, m); 4.1 (1H, m); 5.1 (1H, bs). $^{13}$C NMR (75 MHz, CDCl$_3$, ppm) 8.6; 28.0; 28.3; 28.9; 33.7; 53.0; 79.7; 82.1; 82.6; 155.3; 171.5.

Example 12: Preparation of (R)-2-(t-butoxycarbonylamino)-5-cyanopentanoic acid, t-butyl ester

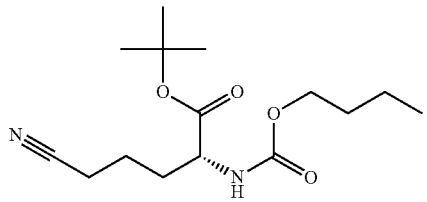 [SMILES: CCCCOC(=O)N[C@H](CCCC#N)C(=O)OC(C)(C)C]

1,2,3,4,5-$^{13}$C$_5$, 2-$^{15}$N—(R)-2-(t-butoxycarbonylamino)-5-iodopentanoic acid, t-butyl ester (21.4 g, 53 mmol) was dissolved in DMSO (50 ml) containing a trace of water and treated with potassium cyanide (5.16 g, 79 mmol) portion wise and stirred at room temperature overnight. Water (200 ml) was added and the product extracted into ethyl acetate. The organic layer was washed with brine and water and shown by TLC to contain a single product (silica gel; 30% ethyl acetate: hexane). The product was concentrated and purified by column chromatography on silica gel, eluting with 10% ethyl acetate/hexane. The fractions containing the target compound were pooled and concentrated under reduced pressure. Yield: 14.75 g (92%).

$^1$H NMR (300 MHz, CDCl$_3$, ppm) 1.47 (9H, s), 1.51 (9H, s), 1.45-2.00 (4H, m), 2.40 (2H, d of quar), 4.19 (1H, d of m), 5.11 (1H, d of d). $^{13}$C NMR (75 MHz, CDCl$_3$, ppm) 17 (d), 21 (t), 32 (t), 53 (m), 171 (d).

5,5-D$_2$-(R)-2-(t-butoxycarbonylamino)-5-iodopentanoic acid, t-butyl ester (21.0 g, 52.3 mmol) was dissolved in DMSO (40 ml) containing a trace of water. Potassium cyanide (5.2 g, 80 mmol) was added portion wise and the mixture stirred at room temperature overnight. The reaction mixture was poured into water (200 ml) and extracted with ethyl acetate. The combined organic extracts were washed with brine, dried over magnesium sulfate and concentrated under reduced pressure. The resulting oil was purified by column chromatography (silica, hexane:ethylacetate 7:3) and isolated as a colorless oil. Yield of 5,5-D$_2$-(R)-2-(t-butoxycarbonylamino)-5-cyanopentanoic acid, t-butyl ester (11.5 g, 73%). $^1$H NMR (300 MHz, CDCl$_3$, ppm) 1,4 (9H, s); 1.5 (9H, s); 1.6 (1H, m); 1.7 (2H, m); 1.9 (1H, m); 4.2 (1H, d); 5.1 (1H, d). $^{13}$C NMR (75 MHz, CDCl$_3$, ppm) 16.4; 21.3; 28.0; 28.3; 32.0; 53.0; 79.9; 82.4; 119.2; 155.4; 171.2

Example 13: Preparation of 5,5,6,6-D$_4$-L-Lysine dihydrochloride salt

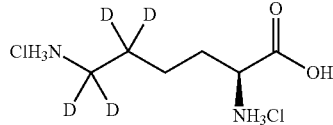

5,5-D$_2$-(R)-2-(t-butoxycarbonylamino)-5-cyanopentanoic acid, t-butyl ester (1 g, 3.33 mmol) was dissolved in D$_4$-acetic acid (25 ml) and PtO$_2$ (80 mg) and Pd/C (10%, 200 mg) added (both catalysts pre-reduced with deuterium) The mixture was deuterogenated at 40 psi for 72 hours. TLC (hexane: ethyl acetate, 1:11) showed completion. The mixture was filtered through celite and concentrated under reduced pressure to give a colorless oil. The product was dissolved in 6M DCl and refluxed for 20 hours. The solvents were removed under reduced pressure and the residue co-evaporated with water (2×20 ml) and ethanol to give 5,5,6, 6-D$_4$-L-lysine dihydrochloride (600 mg, 81%). M/z: 371 (M+H, bistrifluoroacetyl, ethyl ester derivative). Enrichment (by NMR): 98.7%. $^1$H NMR (D$_2$O/TMSP, ppm) 1.6 (2H, m); 2.1 (2H, m); 4.1 (1H, m). $^{13}$C NMR (D$_2$O/TMSP, ppm) 21.1; 29.2; 52.7; 172.1. Other catalysts (such as Raney nickel, Wilkinson's catalyst and platinum oxide or palladium on carbon) may be used for this step. The iodo leaving group gave excellent yields. Bromo, chloro, tosylate and mesylate would all be alternative possibilities.

Example 14: Preparation of 2,3,3,4,4-D5; 3,4,5 13C3 L-Glutamic Acid, N-carbobenzyloxy, 5-methyl ester

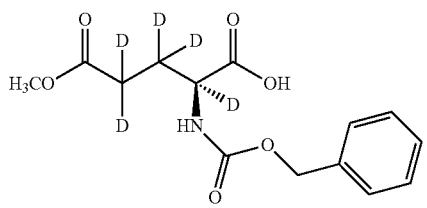 [SMILES: [2H]C([2H])(C(=O)OC)C([2H])([2H])[C@]([2H])(NC(=O)OCc1ccccc1)C(=O)O]

In a 4-necked, 2 L, round bottom flask, equipped with mechanical stirrer, thermometer and a nitrogen inlet and a dropping funnel was suspended powdered L-Glutamic acid, 5-methyl ester (70 g, 0.35 mol.) in 450 mL of 1,4-dioxane. The mixture was stirred for 15 min at room temperature. N-(Benzyloxycarbonyloxy) succinimide (95.2 g, 0.38 mol, 1.1 eq.) was added portion wise. Stirring is continued for 15 min. Triethylamine (106 mL, 0.76 mol., 2.2 eq.), pre-dissolved in 100 mL of 1,4-dioxane was added dropwise to the reaction mixture. The heterogeneous mixture became thicker and stirring was continued for 2-3 h at room temperature.

TLC (EtOH: iPa: NH$_4$OH; 4.5:4.5:1; ninhydrin visualization) shows that the reaction is complete. The reaction pH was adjusted to 3 using 3N HCl. The mixture was concentrated to remove most of the 1,4-dioxane and the resulting aqueous mixture was extracted 5×150 mL with ethyl acetate. The organic layers were washed 10×75 mL with H$_2$O, then concentrated to about ½ volume. The organic solution was washed 2×200 mL with 10% Na$_2$CO$_3$. The aqueous layer (containing the product as sodium salt) was acidified gently with 3N HCl to pH 3. The product was extracted 3×150 mL with EtOAc. The organic layers were combined, dried over MgSO$_4$ then concentrated in vacuum to oil which turns into white solid under overnight vacuum at RT. (96.7 g; 94%). $^1$H and $^{13}$CNMR data show that the material is pure. It will be used in the next step without further purification. $^1$H NMR (300 MHz, CDCl$_3$, ppm) 3.7 (3H, s); 5.1 (2H, s); 5.5 (1H, bs); 7.3 (5H, arom. s). $^{13}$C NMR (75 MHz, CDCl$_3$, ppm) 26.7 (m); 29.4 (m); 51.9; 67.2; 128.1; 128.3; 128.6; 173.3 (m)

Example 15: Preparation of 2,3,3,4,4-D5; 3,4,5 13C3 L-Glutamic acid, N-carbobenzyloxy, 1,-t-butyl ester, 5-methyl ester

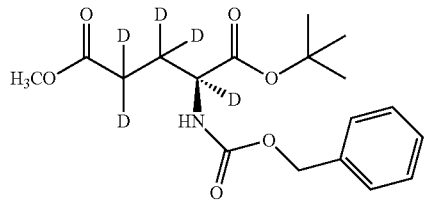 [SMILES: [2H]C([2H])(C(=O)OC)C([2H])([2H])[C@]([2H])(NC(=O)OCc1ccccc1)C(=O)OC(C)(C)C]

An 8 L stainless steel vessel (or pressure proof glass vessel), was charged with L-Glutamic acid, N-carbenzyloxy, 5-methyl ester (96 g, 0.31 mol.), catalytic amount of concentrated H$_2$SO4 (4.5 mL), CH$_2$Cl$_2$ (650 mL) and a stirring bar. The vessel was cooled to −78° C., under nitrogen. Isobutylene gas was liquefied (590 mL, excess, 20 eq.) at −78° C. and transferred into the reaction vessel under nitrogen. The vessel was sealed and the reaction mixture was allowed to warm up to room temperature and the stirring extended for 65 h. A pressure of 25-30 psi was measured on the pressure gauge when room temperature was reached.

TLC (Hexanes: EtOAc, 80:20, UV visualization) taken after 65 h, showed that the conversion has passed 90%. The content of the vessel was gently poured into a 4 L Becker containing 1 L of aqueous 10% Na$_2$CO$_3$ and mixture stirred for 15 min. The mixture was allowed to decant onto a sep-funnel and brine (200 mL) was added to help separate the layers. The aqueous layer was further extracted 3×300 mL with CH$_2$Cl$_2$. The organic layers (milky) were combined and dried over MgSO$_4$ filtered over glass fiber filter paper to yield a clear filtrate. The latter concentrated in vacuum to clear oil. (102 g; 90%). $^1$H and $^{13}$C NMR data show that the material is pure. It will be used in the next step without further purification. $^1$H NMR (300 MHz, CDCl$_3$, ppm) 1.5 (9H, s); 3.7 (3H, s); 5.1 (2H, s); 7.3 (5H, arom. s). $^{13}$C NMR (75 MHz, CDCl$_3$, ppm) 28.3 (m); 29.0 (m); 51.7; 66.9, 82.5; 128.1; 128.2; 128.5; 136.2; 173.3 (d)

Example 16: Preparation of 2,3,3,4,4-D5; 3,4,5 13C3 L-Glutamic Acid, N-t-butoxycarbonyl, 1,-t-butyl ester, 5-methyl ester

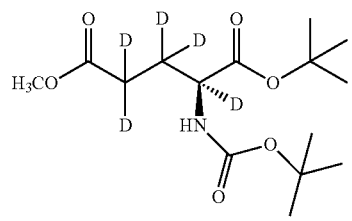 [SMILES: [2H]C([2H])(C(=O)OC)C([2H])([2H])[C@]([2H])(NC(=O)OC(C)(C)C)C(=O)OC(C)(C)C]

L-Glutamic acid, N-carbobenzyloxy, 1,-t-butyl ester, 5-methyl ester (101 g, 0.28 mol.) was dissolved in 1.5 L of methanol. The solution was transferred to an 8 L stainless steel vessel. Boc$_2$O (67.5 g, 0.31 mol., 1.1 eq.) was added in portions to the reaction mixture. 5 g (cat.) of Pd/C (10%) was cautiously added by small portions under N$_2$. The vessel was sealed and pressurized to 60 psi of hydrogen. The vessel was shaken for 2-3 h. A TLC (Hexanes: EtOAc 80:20, KMnO4 visualization) taken after 3 h shows that the reaction is complete. The reaction vessel was vented and $N_2$ was bubbled in the solution for 1 h. Palladium was filtered off through fiber glass filter paper and filtrate was concentrated in vacuum to oil which turns into white solid after 2-3 h of pumping under high vacuum. (95 g, 100%). $^1H$ and $^{13}C$ NMR data show that residual $Boc_2O$ is present but the material is pure enough to be taken to the next step without further purification. $^1H$ NMR (300 MHz, $CDCl_3$, ppm) 1.4 (9H, s); 1.5 (9H, s); 3.7 (3H, s); 5.1 (1H, bs). $^{13}C$ NMR (75 MHz, $CDCl_3$, ppm) 28.3 (m); 29.0 (m); 82.2; 173.4 (d)

The starting materials for the reactions described herein are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

Example 17: Expression and Purification of a Non-Limiting Representative Protein, Serine Hydroxymethyl Transferase (SHMT), Containing the Lysine Isotopologues Described Herein A 20 mL stock culture of M15 cells transformed with the vector pqe30 SHMT are used to inoculate 1 L of medium containing 500 mg alanine, 400 mg arginine, 400 mg aspartic acid, 50 mg cysteine, 400 mg glutamine, 650 mg glutamic acid, 550 mg glycine, 100 mg histidine, 230 mg isoleucine, 230 mg leucine, 420 mg lysine HCl, 250 mg methionine, 130 mg phenylalanine, 100 mg proline, 2.1 g serine, 230 mg threonine, 170 mg tyrosine, 230 mg valine, 500 mg adenine, 650 mg guanosine, 200 mg thymine, 500 mg uracil, 200 mg cytosine, 1.5 g sodium acetate (anhydrous), 1.5 g succinic acid, 750 mg $NH_4Cl$, 850 mg NaOH, 10.5 g $K_2HPO_4$ (anhydrous), 2 mg $CaCl_2$ 2 $xH_2O$, 2 mg $ZnSO_4$ 7 xH2O, 2 mg $MnSO_4H2O$, 50 mg tryptophan, 50 mg thiamine, 50 mg niacin, 1 mg biotin, 20 g glucose, 4 mL 1 M $MgSO_4$, 1 mL 0.01 M $FeCl_3$, 15 mg ampicillin, and 50 mg kanamycin.

When cell density had reached an OD of 1.2, the cells are harvested by centrifugation, rinsed with PBS, recentrifuged and resuspended in a medium of the above proportions but in which the lysine isotopologues described herein, are substituted for the unlabeled lysine. After 30 minutes, protein expression is induced by addition of IPTG to a final concentration of 0.1 mmol. After 6 hours, the cultured cells are centrifuged at 4000 rpm for 20 minutes in a Sorvall RC-3B centrifuge. The cell pellet is then stored at −20 C overnight. The cells are thawed and resuspended in 30 ml of sonication buffer (50 mM sodium phosphate, 500 mM NaCl, pH=8.0). The cells are broken by passing them through a French Press four times at 20,000 psi. The broken cells are subjected to sedimentation at 15,000×g for 20 minutes in Oakridge tubes.

A 5 ml Ni-NTA immobilized metal affinity column is equilibrated in sonication buffer at 5 mL/min. The supernatant (cell lysate) is removed from the Oakridge tube without disturbing the pellet. Cleared lysate is loaded onto the column at 5 mL/min. The column flow-through is saved for later analysis. The material bound to the column then is washed with sonication buffer for 30 minutes until the absorbance of the effluent is less than 0.020. Bound protein is eluted from the column with Elution Buffer (50 mM sodium phosphate, 500 mM NaCl, 500 mM imidizole, pH=8.0) using a single step. The peak fraction is collected manually. A sample of the elution is saved for analysis.

A 300 mL XK-50 column packed with Sephadex G-25 Fine size exclusion chromatography (SEC) resin is equilibrated with anion exchange Buffer A (20 mM Tris HCl, pH=7.5). The Ni-NTA eluate is loaded onto the SEC column at 15 mL/min. The protein peak is collected manually. The protein sample, now in anion exchange Buffer A, is stored at 4 C. during preparation of the next step. A 10 mL Resource Q anion exchange column is equilibrated in Buffer A. The partially purified protein is loaded onto the column at 10 mL/min. The sample is washed with Buffer A for three minutes. The sample is eluted with a linear gradient into Buffer B (20 mM Tris HCl, 1 M NaCl, pH=7.5) over seven minutes. The fractions are collected in 30 second intervals. A sample of each fraction is set aside for analysis.

The material is analyzed by SDS-PAGE using a 12% Tris/Glycine gel at a constant 200 volts for 45 minutes. The pure fractions are loaded into a 3000 MWCO Slidalyzer dialysis cassette. The protein is dialyzed at 4 C. into 50 mM sodium phosphate pH 7.0. Two buffer changes ensure complete removal of the Tris buffer. The final protein concentration is determined using UV absorbance at 280 nm; comparing it to the extinction coefficient for MUP (0.503 at 1 mg/mL). The final concentration of pure Serine Hydroxymethyl Transferase is 48 determined and analyzed by NMR to confirm the incorporation of the lysine isotopologues into this representative protein.

Example 18: Stable Isotopic Labeling by Amino Acids in Cell Culture

The exemplified heavy lysines may be used to prepare cell cultures in which natural lysine has been replaced by heavy lysines. The resulting proteins and protein fragments, obtained by lysis with trypsin or lysC, may be differentiated on the basis of their exact masses using a mass spectrometer of sufficient resolving power, even though the heavy lysines have the same gross mass. The exemplified lysines may therefore be used to expand the multiplexing beyond that available by using lysines with different gross mass differences.

In a typical experiment a cell line will be initiated in a regular medium and sub-cultures seeded and grown on a custom medium devoid of protein and natural lysine but each enriched with one of the heavy lysines. See, for example, the methods of Kruger et al., 2008 Cell 134, 353-364. The cell lines are allowed to multiply and are harvested. The proteins fractions from each of the cell lines used are separated and, after appropriate pretreatment, are lysed using typsin or lysC to cleave proteins at lysine sites. Protein fragments are obtained containing heavy lysines mixed with natural lysine. By selecting for exact mass differences in the mass spectrometric analysis of the mixed protein fragments, relevant proteins may be identified.

In an alternative procedure, one or more of the cell lines may be subjected to perturbation by treatment with a drug or other substance or condition leading to a biological effect. The resulting changes in protein concentrations may be identified using the outline procedure described above, identifying proteins controlling or affected by the perturbation.

In another alternative procedure, a group of cell lines associated with a particular condition (such as cancer) may be cultured. After growth, the cells may be washed to free them of protein associated with the growth medium and cultured in a protein free medium containing natural amino acids excluding natural lysine and including one or more of the heavy lysines exemplified. The cells are then harvested, combined and subjected to lysis as described above. The protein fragments thus obtained may serve as spike-in reference standards to identify proteins associated with the particular condition. Changes in protein concentrations resulting from perturbations of cell lines grown with natural lysine or obtained from normal or diseased individuals or animals may also be identified by mass spectrometric analysis as described above.

Example 19: Preparation and Use of Mouse Chow Containing Exemplified Lysines

Mouse chows containing natural and exemplified lysines are prepared as described below and samples taken as desired. After processing, protein fragments containing natural and exemplified lysines are obtained and compared by mass spectrometry, using instrumentation capable of differentiating the exact mass difference between the different exemplified lysines. Using such instrumentation protein fragments with exact mass differences may be selected for analysis and the proteins identified. In another modification of the procedure, one or more group of mice fed with the exemplified lysines may be subjected to perturbation, by, for example, treatment with a drug or other species or condition that modifies biological function and changes in protein concentration in blood or organs may be identified.

Preparation of Mouse Chow

A customized lysine-free mouse diet (for example Harlan-Teklad, TD.99386) is combined with one of the exemplified heavy L-lysines to a final concentration of 1%. To obtain a homogeneous distribution of the amino acid, the powder is vigorously mixed with a blender for 5 minutes. For the preparation of food pellets, approximately 10 g of the mixture is filled into a manufacturing cylinder with an inner diameter of approximately 1.5 cm and a length of approximately 10 cm or similar device. The mouse chow is compressed with an exactly fitting pestle for 1 minute. Pellets are taken out and dried overnight at room temperature. After drying, the pellets are cut into smaller pieces. A similar process is used to prepare individual mouse chows containing other exemplified heavy lysines and natural L-lysine.

The lysine content is checked by an appropriate method (such as Moore et al., Fed Proc. 1958, 17, 1107-1115) against the mouse chow containing natural L-lysine to confirm a comparable incorporation of the lysines in all diets.

Feeding Mice

Separate groups of mice are fed ad libitum separately with a control diet, the diet containing natural lysine and the diets containing heavy lysines. Each group is provided with water ad libitum. Weight gain and food consumption is monitored against the group fed with the control diet. Mice may be used in experimentation either after a few weeks of feeding or after several generations depending on the degree of incorporation required.

Sampling

Blood:

Mice are anesthetized with isofluran or similar anesthetic, and an appropriate volume of blood (such as 20 μl) is taken from the retro-orbital plexus or other source. Blood samples are incubated with heparin (20 U/ml) and, after centrifugation, the supernatant is frozen in liquid nitrogen and stored at −80° C.

Tissue Harvest:

Animals are sacrificed by cervical dislocation or other appropriate method, tissues are dissected, washed in phosphate-buffered saline (PBS [pH 7.4]) or equivalent, and frozen in liquid nitrogen. For protein isolation, tissues are homogenized in a buffer and protease inhibitors. The lysates are centrifuged and assayed to determine protein concentrations of the supernatants.

Mitochondria Isolation:

Liver tissue is quickly washed in water, and then washed three times in buffer containing protease inhibitors and isolated according a procedure such as that described in Forner et al., Cell Proteomics, 2006, 5, 522-533 and purified by density centrifugation.

Such methods can be adapted by the skilled artisan for large scale production of numerous proteins that can be incorporated into animal feed, e.g., mouse or rat chow.

From the foregoing it will be appreciated that, although specific embodiments of the invention have been described herein for purposes of illustration, various modifications may be made without deviating from the spirit and scope of the invention.

Throughout the description as described herein, reference is made to various patent applications and publications, each of which are herein incorporated by reference in their entirety.

What is claimed is:

1. A compound of Formula I-A

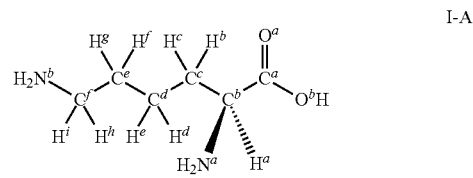

I-A or a salt thereof, wherein:

each $H^a$, $H^b$, $H^c$, $H^d$, $H^e$, $H^f$, $H^g$, $H^h$, and $H^i$ is independently $^1H$ or $^2H$;

each $C^a$, $C^b$, $C^c$, $C^d$, $C^e$ and $C^f$ is independently $^{12}C$ or $^{13}C$; and at least two of $C^a$, $C^b$, $C^c$, $C^d$, $C^e$ and $C^f$ are $^{13}C$;

each $N^a$ and $N^b$ is independently $^{14}N$ or $^{15}N$; and $O^a$ and $O^b$ are both $^{18}O$;

with the provision that the compound is not:

2,3,3,4,4,5,5,6,6-$D_9$-L-Lysine;

3,3,4,4,5,5,6,6-$D_8$-L-Lysine;

1,2,3,4,5,6-$^{13}C_6$-L-Lysine;

1,2,3,4,5,6-$^{13}C_6$,$^{15}N_2$-L-Lysine;

4,4,5,5-$D_4$-L-Lysine or 1,2-$^{13}C_2$-L-Lysine.

2. The compound of claim 1, wherein $C^c$, $C^d$ and $C^e$ are $^{13}C$.

3. The compound of claim 1, wherein at least four of $C^a$, $C^b$, $C^c$, $C^d$, $C^e$ and $C^f$ are $^{13}C$.

4. The compound of claim 1, wherein $C^b$, $C^c$, $C^d$ and $C^e$ are $^{13}C$.

5. The compound of claim 1, wherein $C^c$, $C^d$, $C^e$ and $C^f$ are $^{13}C$.

6. The compound of claim 1, wherein at least five of $C^a$, $C^b$, $C^c$, $C^d$, $C^e$ and $C^f$ are $^{13}C$.

7. The compound of claim 1, wherein $C^a$, $C^b$ $C^d$ and $C^e$ are $^{13}C$.

8. The compound of claim 1, wherein $C^b$, $C^c$, $C^d$, $C^e$ and $C^f$ are $^{13}C$.

9. The compound of any one of claims 1-8, wherein at least two of $H^a$, $H^b$, $H^c$, $H^d$, $H^e$, $H^f$, $H^g$, $H^h$ and $H^i$ are $^2H$.

10. The compound of any one of claims 1-8, wherein $H^g$ and $H^f$ are $^2H$.

11. The compound of any one of claims 1-8, wherein $H^h$ and $H^i$ are $^2H$.

12. The compound of any one of claims 1-8, wherein at least four of $H^a$, $H^b$, $H^c$, $H^d$, $H^e$, $H^f$, $H^g$, $H^h$ and $H^i$ are $^2H$.

13. The compound of any one of claims 1-8, wherein $H^f$, $H^g$, $H^h$ and $H^i$ are $^2H$.

14. The compound of any one of claims 1-8, wherein at least six of $H^a$, $H^b$, $H^c$, $H^d$, $H^e$, $H^f$, $H^g$, $H^h$ and $H^i$ are $^2H$.

15. The compound of any one of claims 1-8, wherein $N^a$ is $^{15}N$.

16. The compound of any one of claims 1-8, wherein $N^b$ is $^{15}N$.

17. The compound of any one of claims 1-8, wherein $N^a$ and $N^b$ are $^{15}N$.

18. The compound of claim 1, wherein the compound is of Formula II

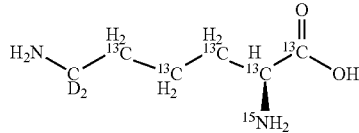

or a salt thereof.

19. The compound of claim 1, wherein the compound is of Formula III

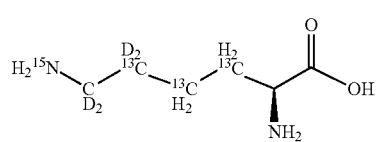

or a salt thereof.

20. The compound of claim 1, wherein the compound is of Formula IV

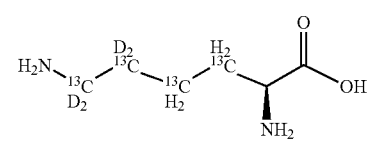

or a salt thereof.

21. The compound of claim 1, wherein the compound is of Formula V

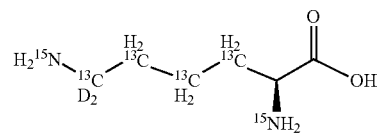

or a salt thereof.

* * * * *